(12) United States Patent
Alcaraz et al.

(10) Patent No.: US 7,956,070 B2
(45) Date of Patent: *Jun. 7, 2011

(54) PIPERIDINES AS CHEMOKINE MODULATORS (CCR)

(75) Inventors: Lilian Alcaraz, Loughborough (GB); Peter Cage, Loughborough (GB); Mark Furber, Loughborough (GB); Elizabeth Kinchin, Loughborough (GB); Christopher Luckhurst, Loughborough (GB); Aaron Rigby, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 1166 days.

This patent is subject to a terminal disclaimer.

(21) Appl. No.: 10/587,633

(22) PCT Filed: Jan. 31, 2005

(86) PCT No.: PCT/SE2005/000110
§ 371 (c)(1),
(2), (4) Date: Jul. 28, 2006

(87) PCT Pub. No.: WO2005/073192
PCT Pub. Date: Aug. 11, 2005

(65) Prior Publication Data
US 2007/0054924 A1    Mar. 8, 2007

(30) Foreign Application Priority Data
Feb. 2, 2004  (SE) .................................... 0400208-5

(51) Int. Cl.
*A61K 31/44* (2006.01)
*C07D 417/12* (2006.01)

(52) U.S. Cl. ........ 514/326; 514/249; 514/269; 514/307; 514/318; 514/323; 546/141; 546/193; 546/201; 546/209; 546/210

(58) Field of Classification Search .................. 514/249, 514/269, 307, 318, 323, 326; 544/315, 353; 546/141, 193, 201, 210, 209
See application file for complete search history.

(56) References Cited

U.S. PATENT DOCUMENTS

| | | | |
|---|---|---|---|
| 5,935,974 A | 8/1999 | Rae et al. | |
| 6,124,319 A | 9/2000 | MacCoss et al. | |
| 6,140,349 A | 10/2000 | Caldwell et al. | |
| 6,166,037 A | 12/2000 | Budhu et al. | |
| 6,331,541 B1 | 12/2001 | Ko et al. | |
| 6,358,979 B1 | 3/2002 | Finke et al. | |
| 6,444,686 B1 | 9/2002 | Ko et al. | |
| 6,489,354 B1 | 12/2002 | Bao et al. | |
| 6,566,376 B1 | 5/2003 | Baxter et al. | |
| 6,605,623 B1 | 8/2003 | Ko et al. | |
| 6,627,629 B2 | 9/2003 | Ko et al. | |
| 7,265,227 B2 | 9/2007 | Evans et al. | |
| 7,709,500 B2 | 5/2010 | Alcaraz et al. ................ 514/318 |
| 2005/0107428 A1 | 5/2005 | Alcaraz et al. | |
| 2007/0054924 A1 | 3/2007 | Alcaraz et al. | |
| 2008/0108661 A1 | 5/2008 | Cage et al. | |

FOREIGN PATENT DOCUMENTS

| | | |
|---|---|---|
| EP | 0903349 | 3/1999 |
| WO | WO9710207 | 3/1997 |
| WO | WO9723458 | 7/1997 |
| WO | WO9818761 | 5/1998 |
| WO | WO 99/04794 | 2/1999 |
| WO | WO0012478 | 3/2000 |
| WO | WO0029377 | 5/2000 |
| WO | WO 00/31033 | 6/2000 |
| WO | WO0035449 | 6/2000 |
| WO | WO0035451 | 6/2000 |
| WO | WO0035452 | 6/2000 |
| WO | WO0035453 | 6/2000 |
| WO | WO0035454 | 6/2000 |
| WO | WO 00/58305 | 10/2000 |
| WO | WO0102381 | 1/2001 |
| WO | WO 01/62728 | 8/2001 |
| WO | WO 01/62729 | 8/2001 |
| WO | WO0162757 | 8/2001 |
| WO | WO0177101 | 10/2001 |
| WO | WO0198269 | 12/2001 |
| WO | WO0198270 | 12/2001 |
| WO | WO 02/20484 | 3/2002 |
| WO | WO 02/30899 | 4/2002 |
| WO | WO 02/039125 | 5/2002 |
| WO | WO0250070 | 6/2002 |
| WO | WO 03/018556 | 3/2003 |
| WO | WO 03/068743 | 8/2003 |
| WO | WO 03/082190 | 10/2003 |
| WO | WO 2005/073192 | 8/2005 |
| WO | WO2007/114770 | 10/2007 |

OTHER PUBLICATIONS

Rollins "Chemokines" Blood, v.90(3)p. 909-928 (1997).*
Cohen et al. "Cytokine function . . . " CA 125:31527 (1996).*
Braga et al. "Making crystals . . . " J. Royal. soc. Chem. Chem. Commun. p. 3635-3645 (2005).*
Kenner et al. "acylation of . . . " CA50:8632 (1956).*
Kensende "Hydrogen bonding and . . . " CA96:34416 (1982).*
Boskabady et al. "The effect of exposure . . . " Pathophysiology v.14, p. 97-104 (2007).*
Barnes, "Cytokine-directed therapies for the treatment of chronic airway diseases",*Cytokine & Growth Factor Reviews* 14:511-522 (2003).
Boskabady and Kiani, "The Effect of Exposure of Guinea Pig to Cigarette Smoke and their Sensitization in Tracheal Responsiveness to Histamine and Histamine Receptor ($H_1$) Blockade by Chlorpheniramine", *Pathophysiology* 14:97-104 (2007).
Cohen et al., "Cytokine function: A study in biologic diversity", *CAPLUS* 125:31527 (1996).

(Continued)

*Primary Examiner* — Celia Chang
(74) *Attorney, Agent, or Firm* — Fish & Richardson P.C.

(57) ABSTRACT

Compounds of formula (I):

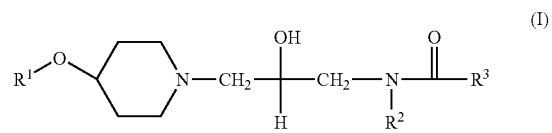

are modulators of chemokine (for example CCR3) activity (for use in, for example, treating asthma).

2 Claims, No Drawings

OTHER PUBLICATIONS

King, "Bioisosteres, Conformational Restriction, and Pro-drugs—Case History: An Example of a Conformational Restriction Approach", *Medicinal Chemistry: Principles and Practice* pp. 206-209 (1994).
Patani et al., "Bioisosterism: A Rational Approach in Drug Design", *Chem. Rev.* 96:3147-3148, 3170 (1996).
Rollins, "Chemokines", *Blood* 90(3):909-928 (1997).
Hodgson et al., "Chemokines and Drug Discovery", *Drug News Perspect* 17(5):335-338 (2004).
Baggiolini, M., "Chemokines in pathology and medicine", *Journal of Internal Medicine* 250:91-104 (2001).
Gould, "Salt selection for basic drugs", *International Journal of Pharmaceutics* 33:201-217 (1986).
USPTO Non-Final Office Action in U.S. Appl. No. 11/866,611, mailed Jun. 15, 2009, 25 pages.
International Search Report.

* cited by examiner

PIPERIDINES AS CHEMOKINE MODULATORS (CCR)

CROSS-REFERENCE TO RELATED APPLICATIONS

This application is a national phase application under 35 U.S.C. §371 of PCT International Application No. PCT/SE2005/000110, filed Jan. 31, 2005, which claims priority to Swedish Application Serial No. 0400208-5, tiled Feb. 2, 2004.

The present invention concerns piperidine derivatives having pharmaceutical activity, to processes for preparing such derivatives, to pharmaceutical compositions comprising such derivatives and to the use of such derivatives as active therapeutic agents.

Pharmaceutically active N-(2-hydroxyprop-1-yl)piperidine derivatives are disclosed in WO 03/068743.

Histamine is a basic amine, 2-(4-imidazolyl)-ethylamine, and is formed from histidine by histidine decarboxylase. It is found in most tissues of the body, but is present in high concentrations in the lung, skin and in the gastrointestinal tract. At the cellular level inflammatory cells such as mast cells and basophils store large amounts of histamine. It is recognised that the degranulation of mast cells and basophils and the subsequent release of histamine is a fundamental mechanism responsible for the clinical manifestation of an allergic process. Histamine produces its actions by an effect on specific histamine G-protein coupled receptors, which are of three main types, H1, H2 and H3. Histamine H1 antagonists comprise the largest class of medications used in the treatment of patients with allergic disorders, for example rhinitis and urticaria. Antagonists of H1 are useful in controlling the allergic response by for example blocking the action of histamine on post-capillary venule smooth muscle, resulting in decreased vascular permeability, exudation and oedema. The antagonists also produce blockade of the actions of histamine on the H1 receptors on c-type nociceptive nerve fibres, resulting in decreased itching and sneezing.

Chemokines are chemotactic cytokines that are released by a wide variety of cells to attract macrophages, T cells, eosinophils, basophils and neutrophils to sites of inflammation and also play a role in the maturation of cells of the immune system. Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterised by a conserved four cysteine motif. The chemokine superfamily can be divided into two main groups exhibiting characteristic structural motifs, the Cys-X-Cys (C—X—C, or α) and Cys-Cys (C—C, or β) families. These are distinguished on the basis of a single amino acid insertion between the NH-proximal pair of cysteine residues and sequence similarity.

The C—X—C chemokines include several potent chemoattractants and activators of neutrophils such as interleukin-8 (IL-8) and neutrophil-activating peptide 2 (NAP-2).

The C—C chemokines include potent chemoattractants of monocytes and lymphocytes, but not neutrophils, such as human monocyte chemotactic proteins 1-3 (MCP-1, MCP-2 and MCP-3), RANTES (Regulated on Activation, Normal T Expressed and Secreted), eotaxins and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

Viral infections are known to cause lung inflammation. It has been shown experimentally that the common cold increases mucosal output of eotaxin in the airways. Instillation of eotaxin into the nose can mimic some of the signs and symptoms of a common cold. (See, Greiff L et al Allergy (1999) 54(11) 1204-8 [Experimental common cold increase mucosal output of eotaxin in atopic individuals] and Kawaguchi M et al Int. Arch. Allergy Immunol. (2000) 122 S1 44 [Expression of eotaxin by normal airway epithelial cells after virus A infection].)

The compounds of the present invention are useful in the treatment of CCR3 mediated disease states (such as asthma and/or rhinitis) and show good specificity (for example 100-fold difference in activity) for the CCR3 receptor over other receptors present in a mammal such as G-Protein Coupled Receptors (for example: alpha 1 adrenoceptor and $5HT_{2B}$ receptors) and ion channels (for example: the human ether-a-go-go-related gene (hERG) potassium channel).

The present invention provides a compound of formula (I):

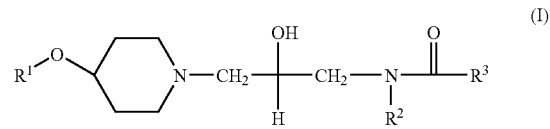

wherein:
$R^1$ is phenyl optionally substituted by halogen, cyano, $C_{1-4}$ alkyl or $C_{1-4}$ haloalkyl;
$R^2$ is hydrogen, $C_{1-6}$ alkyl or $C_{3-6}$ cycloalkyl; and,
$R^3$ is a group having an NH or OH that has a calculated or measured pKa of 1.0 to 8.0; or a pharmaceutically acceptable salt.

Certain compounds of the present invention can exist in different isomeric forms (such as enantiomers, diastereomers, geometric isomers or tautomers). The present invention covers all such isomers and mixtures thereof in all proportions.

Suitable salts include acid addition salts such as a hydrochloride, dihydrochloride, hydrobromide, phosphate, sulfate, acetate, diacetate, fumarate, maleate, tartrate, citrate, oxalate, methanesulfonate or p-toluenesulfonate. Salts also include metal salts, such as an alkali metal salt (for example a sodium or potassium salt) or an alkaline earth metal salt (for example magnesium or calcium).

The compounds of the invention may exist as solvates (such as hydrates) and the present invention covers all such solvates.

The pKa of a compound of formula (I) is calculated using ACD/Labs 6.00 software available from Advanced Chemistry Development Inc, 90 Adelaide Street, West Toronto, Ontario, Canada. The pKa of a compound of formula (I) is measured using one of the methodologies recited below.

Halogen is, for example fluorine or chlorine.

Alkyl groups and moieties are straight or branched chain and are, for example, methyl, ethyl, n-propyl, iso-propyl or tert-butyl.

Cycloalkyl is monocyclic and is, for example, cyclopropyl, cyclopentyl or cyclohexyl.

Haloalkyl is an alkyl group carrying one or more (such as 1 to 6) halogen (such as chloro or fluoro atoms) and is, for example, $CF_3$, $CH_2CF_3$ or $C_2F_5$.

Fluoroalkyl is an alkyl group carrying one or more (such as 1 to 6) fluoro atoms and is, for example, $CH_2F$, $CF_3$, $CH_2CF_3$ or $C_2F_5$.

In one aspect the present invention provides a compound of formula (I) wherein $R^1$ is phenyl optionally substituted by halogen, cyano or $C_{1-4}$ alkyl.

In another aspect the present invention provides a compound of formula (I) wherein $R^1$ is phenyl substituted with one, two or three of: halogen (such as fluoro or chloro), cyano or $C_{1-4}$ alkyl (such as methyl); for example $R^1$ is phenyl substituted by one, two or three of: fluoro, chloro, methyl or cyano. In another aspect $R^1$ is phenyl substituted by one, two or three (such as two or three) of: fluoro, chloro, cyano or methyl (such as chloro, cyano or methyl). $R^1$ is, for example, 3,4-dichlorophenyl, 2-methyl-3-chloro-4-cyanophenyl, 2-methyl-4-chlorophenyl, 3-methyl-2,4-dichlorophenyl, 2-methyl-3,4-dichlorophenyl, 3-chloro-4-cyanophenyl, 3,4-difluorophenyl, 3-fluoro-4-chlorophenyl or 4-chlorophenyl (such as 2-methyl-4-chlorophenyl, 3-methyl-2,4-dichlorophenyl, 2-methyl-3,4-dichlorophenyl, 3-chloro-4-cyanophenyl, 3,4-difluorophenyl, 3-fluoro-4-chlorophenyl or 4-chlorophenyl). In a still further aspect $R^1$ is 3,4-dichlorophenyl or 3-chloro-4-cyanophenyl.

In a further aspect of the invention $R^1$ is phenyl substituted by one or more of chloro or methyl and optionally further substituted by fluoro. For example $R^1$ is 2-methyl-4-chlorophenyl, 3-methyl-2,4-dichlorophenyl, 2-methyl-3,4-dichlorophenyl, 3-fluoro-4-chlorophenyl, 4-chlorophenyl or 3,4-dichlorophenyl.

In another aspect of the invention $R^1$ is 3,4-dichlorophenyl, 2-methyl-4-chlorophenyl, 3-methyl-2,4-dichlorophenyl, 2-methyl-3,4-dichlorophenyl or 2-methyl-3-chloro-4-cyanophenyl.

In a still further aspect the present invention provides a compound of formula (I) wherein $R^2$ is hydrogen or $C_{1-4}$ alkyl (such as methyl).

In yet another aspect of the invention $R^2$ is hydrogen.

The acidic NH (that is the NH having a calculated or measured pKa of 1.0 to 8.0) of $R^3$ can be part of a ring or it can be part of a substituent on an aryl or heterocyclyl ring. The acidic OH (that is the OH having a calculated or measured pKa of 1.0 to 8.0) of $R^3$ can be a substituent or part of a substituent (such an OH in a carboxylic acid group) on an aryl or heterocyclyl ring. Thus, for example, the acidic OH of $R^3$ can be part of an acidic phenol, in a carboxylic acid, or in a hydroxy aromatic heterocyclyl (such as a hydroxypyridine which may tautomerise to a pyridone).

Aryl includes optionally substituted phenyl and naphthyl.

Heterocyclyl is an optionally substituted aromatic or non-aromatic 5- or 6-membered ring, comprising, as required, at least one heteroatom selected from the group comprising nitrogen, oxygen and sulphur; or an N-oxide thereof, or an S-oxide or S-dioxide thereof. Heterocyclyl is, for example, furyl, thienyl (also known as thiophenyl), pyrrolyl, 2,5-dihydropyrrolyl, thiazolyl (for example in 2-oxo-2,3-dihydro-1,3-thiazolyl), isothiazolyl, pyrazolyl, oxazolyl, isoxazolyl, imidazolyl, triazolyl (for example in 1H-1,2,3-triazolyl), pyridinyl (for example in 6-oxo-1,6-dihydro-pyridinyl) or pyrimidinyl.

In an aspect of the present invention the acidic NH of $R^3$ is part of a suitably substituted ring (for example part of a pyrrolyl, 2,5-dihydropyrrolyl, thiazolyl, isothiazolyl, pyrazolyl, oxazolyl, isoxazolyl, imidazolyl, triazolyl, pyridinyl or pyrimidinyl ring) or part of a substituent on a suitably substituted aryl (for example phenyl or naphthyl) or suitably substituted heterocyclyl (for example furyl, thienyl, pyrrolyl, 2,5-dihydropyrrolyl, thiazolyl, isothiazolyl, pyrazolyl, oxazolyl, isoxazolyl, imidazolyl, triazolyl, pyridinyl or pyrimidinyl) ring.

In another aspect of the present invention the acidic OH of $R^3$ is a substituent or part of a substituent (such an OH in a carboxylic acid group) on a suitably substituted aryl (for example phenyl or naphthyl) or suitably substituted heterocyclyl (for example furyl, thienyl, pyrrolyl, 2,5-dihydropyrrolyl, thiazolyl, isothiazolyl, pyrazolyl, oxazolyl, isoxazolyl, imidazolyl, triazolyl, pyridinyl or pyrimidinyl) ring. Thus, for example, the acidic OH of $R^3$ can be part of an acidic phenol (substituted or unsubstituited), in a carboxylic acid, or in a suitably substituted hydroxy aromatic heterocyclyl (such as a hydroxypyridine which may tautomerise to a pyridone). Further examples of suitably substituted hydroxy aromatic heterocyclyl are hydroxyquinolines, hydroxyisoquinolines and hydroxybenzimidazoles.

In one aspect of the present invention when the acidic NH of $R^3$ is part of a suitably substituted ring it is, for example, part of a 2-oxo-thiazol-5-yl, 2-oxo-oxazol-5-yl, 2-oxo-imidazol-5-yl, 1H-1,2,3-triazol-4-yl, 4-oxo-1H-1,4-dihydropyridin-3-yl, 2,6-dioxo-1H-1,2,3,6-tetrahydropyrimidin-4-yl, 6-oxo-1H-1,6-dihydropyridin-3-yl or 2H-tetrazol-5-yl ring.

In another aspect of the present invention when the acidic NH of $R^3$ is part of a suitably substituted ring it is, for example, part of a 2-oxo-thiazol-5-yl, 1H-1,2,3-triazol-4-yl or 6-oxo-1H-1,6-dihydropyridin-3-yl ring.

In a further aspect of the present invention when the acidic NH of $R^3$ is part of a substituent it is, for example, part of $NHS(O)_2(C_{1-4}$ alkyl).

In another aspect the present invention provides a compound of formula (I) wherein $R^3$ is a group having an NH or OH that has a calculated or measured pKa of 3 to 6.5.

In yet another aspect the present invention provides a compound of formula (I) wherein $R^3$ is a group having an NH or OH that has a calculated or measured pKa of 1.0 to 8.0 (for example 3 to 6.5), the group $R^3$ being, for example, 2-oxo-thiazol-5-yl having a suitable electron withdrawing substituent {such as $C_{1-4}$ fluoroalkyl (for example $CF_3$, $CH_2CF_3$ or $C_2F_5$), an aryl group (for example 4-fluorophenyl), a heterocyclyl group (for example pyridyl) or a group $CH_2S(O)_2(C_{1-4}$ alkyl)} in the 4-position;

2-oxo-oxazol-5-yl having a suitable electron withdrawing substituent {such as $C_{1-4}$ fluoroalkyl (for example $CF_3$, $CH_2CF_3$ or $C_2F_5$) or $CH_2S(O)_2(C_{1-4}$ alkyl)} in the 4-position;

1H-1,2,3-triazol-4-yl having a suitable substituent {such as $C_{1-4}$ alkyl (for example $CH_3$ or $CH(CH_3)_2$), $C_{3-6}$ cycloalkyl (for example cyclopropyl), $C_{1-4}$ fluoroalkyl (for example $CF_3$, $CH_2CF_3$ or $C_2F_5$), S—$R^4$ (wherein $R^4$ is $C_{1-4}$ alkyl [for example $CH_3$], $C_{1-4}$ fluoroalkyl [for example $CF_3$, $CH_2CF_3$ or $C_2F_5$] or $C_{3-6}$ cycloalkyl [for example cyclopropyl]), $NHS(O)_2(C_{1-4}$ alkyl), $N(C_{1-4}$ alkyl)$S(O)_2(C_{1-4}$ alkyl), an aryl group (for example 4-fluorophenyl), a heterocyclyl group (for example pyridyl) or a group $CH_2S(O)_2(C_{1-4}$ alkyl)} in the 5-position;

4-oxo-1H-1,4-dihydropyridin-3-yl having a suitable electron withdrawing substituent {such as $C_{1-4}$ fluoroalkyl (for example $CF_3$ of $C_2F_5$)} in the 2-position;

2,6-dioxo-1H-1,2,3,6-tetrahydropyrimidin-4-yl having a suitable substituent {such as $C_{1-4}$ alkyl (for example $CH_3$), $C_{3-6}$ cycloalkyl (for example cyclopropyl) or $CH_2$ ($C_{1-3}$ fluoroalkyl) (for example $CH_2CF_3$)} in the 3-position and optionally substituted in one or more other ring positions;

6-oxo-1H-1,6-dihydropyridin-3-yl having a suitable electron withdrawing substituent {such as $C_{1-4}$ fluoroalkyl (for example $CF_3$, $CH_2CF_3$ or $C_2F_5$), cyano or phenyl} in the 2-position and/or the 5-position and optionally substituted in one or more other ring positions;

6-oxo-1H-1,6-dihydropyridin-3-yl having $CH_2CO_2H$ on the ring nitrogen and optionally substituted in one or more other ring positions;

2H-tetrazol-5-yl;

a $CO_2H$, $CH_2CO_2H$ or $OCH_2CO_2H$ group on an optionally substituted phenyl, optionally substituted $CH_2O$phenyl, optionally substituted naphthyl ring or optionally substituted acylated (such as with $C(O)(C_{1-4}$ alkyl)) dihydroisoquinolinyl ring; or, an $NHS(O)_2(C_{1-4}$ alkyl) (for example $NHS(O)_2CH_3$) group on an optionally substituted aromatic heterocyclyl ring (for example pyridinyl, pyrimidinyl or thiazolyl);

or, where possible, a tautomer thereof.

In one aspect of the invention acylated (such as with $C(O)(C_{1-4}$ alkyl)) dihydroisoquinolinyl carries the $CO_2H$, $CH_2CO_2H$ or $OCH_2CO_2H$ group on position 7.

In yet another aspect the present invention provides a compound of formula (I) wherein $R^3$ is a group having an NH or OH that has a calculated or measured pKa of 1.0 to 8.0 (for example 3 to 6.5), the group $R^3$ being, for example, 2-oxo-thiazol-5-yl having a suitable electron withdrawing substituent {such as $C_{1-4}$ fluoroalkyl (for example $CF_3$, $CH_2CF_3$ or $C_2F_5$), an aryl group (for example 4-fluorophenyl), a heterocyclyl group (for example pyridyl) or a group $CH_2S(O)_2(C_{1-4}$ alkyl)} in the 4-position;

2-oxo-oxazol-5-yl having a suitable electron withdrawing substituent {such as $C_{1-4}$ fluoroalkyl (for example $CF_3$, $CH_2CF_3$ or $C_2F_5$) or $CH_2S(O)_2(C_{1-4}$ alkyl)} in the 4-position;

1H-1,2,3-triazol-4-yl having a suitable substituent {such as $C_{1-4}$ alkyl (for example $CH_3$), $C_{3-6}$ cycloalkyl (for example cyclopropyl), $C_{1-4}$ fluoroalkyl (for example $CF_3$, $CH_2CF_3$ or $C_2F_5$), S—$R^4$ (wherein $R^4$ is $C_{1-4}$ alkyl [for example $CH_3$], $C_{1-4}$ fluoroalkyl [for example $CF_3$, $CH_2CF_3$ or $C_2F_5$] or $C_{3-6}$ cycloalkyl [for example cyclopropyl]), $NHS(O)_2(C_{1-4}$ alkyl), an aryl group (for example 4-fluorophenyl), a heterocyclyl group (for example pyridyl) or a group $CH_2S(O)_2(C_{1-4}$ alkyl)} in the 5-position;

4-oxo-1H-1,4-dihydropyridin-3-yl having a suitable electron withdrawing substituent {such as $C_{1-4}$ fluoroalkyl (for example $CF_3$ of $C_2F_5$)} in the 2-position;

2,6-dioxo-1H-1,2,3,6-tetrahydropyrimidin-4-yl having a suitable substituent {such as $C_{1-4}$ alkyl (for example $CH_3$), $C_{3-6}$ cycloalkyl (for example cyclopropyl) or $CH_2$ ($C_{1-3}$ fluoroalkyl) (for example $CH_2CF_3$)} in the 3-position;

6-oxo-1H-1,6-dihydropyridin-3-yl having a suitable electron withdrawing substituent {such as $C_{1-4}$ fluoroalkyl (for example $CF_3$, $CH_2CF_3$ or $C_2F_5$) or cyano} in the 2-position or the 5-position and optionally substituted in other positions;

2H-tetrazol-5-yl;

a $CO_2H$ group on an optionally substituted phenyl or naphthyl ring; or, an $NHS(O)_2(C_{1-4}$ alkyl) (for example $NHS(O)_2CH_3$) group on an optionally substituted aromatic heterocyclyl ring (for example pyridinyl, pyrimidinyl or thiazolyl);

or, where possible, a tautomer thereof.

Where indicated above that a heterocyclyl ring in $R^3$ may be optionally substituted it can be optionally substituted by, for example: fluoro, chloro, bromo, $C_{1-4}$ alkyl (for example methyl), $C_{3-6}$ cycloalkyl (for example cyclopropyl), $C_{1-4}$ fluoroalkyl (for example $CF_3$, $CH_2CF_3$ or $C_2F_5$), S—$R^4$ (wherein $R^4$ is $C_{1-4}$ alkyl [for example $CH_3$], $C_{1-4}$ fluoroalkyl [for example $CF_3$, $CH_2CF_3$ or $C_2F_5$] or $C_{3-6}$ cycloalkyl [for example cyclopropyl]), cyano, $S(O)_2(C_{1-4}$ alkyl) (for example $S(O)_2CH_3$) or $S(O)_2NH(C_{1-4}$ alkyl) (for example $S(O)_2NHCH_3$).

Where indicated above that a phenyl or naphthyl ring in $R^3$ may be optionally substituted it can be optionally substituted by, for example, halogen, cyano, $C_{1-4}$ alkyl, $C_{1-4}$ alkoxy, $C_{1-4}$ fluoroalkyl (for example $CF_3$, $CH_2CF_3$ or $C_2F_5$)}, $OCF_3$, $SCF_3$, nitro, $S(C_{1-4}$ alkyl), $S(O)(C_{1-4}$ alkyl), $S(O)_2(C_{1-4}$ alkyl), $S(O)_2NH(C_{1-4}$ alkyl), $S(O)_2N(C_{1-4}$ alkyl)$_2$, $NHC(O)(C_{1-4}$ alkyl), $NHS(O)_2(C_{1-4}$ alkyl).

In one aspect of the invention $R^3$ is 2-oxo-thiazol-5-yl having $C_{1-4}$fluoroalkyl (for example $CF_3$, $CH_2CF_3$ or $C_2F_5$) in the 4-position;

1H-1,2,3-triazol-4-yl having a suitable substituent {such as $C_{1-4}$ alkyl (for example $CH_3$) or S—$R^4$ (wherein $R^4$ is $C_{1-4}$ fluoroalkyl [for example $CF_3$, $CH_2CF_3$ or $C_2F_5$])} in the 5-position;

2,6-dioxo-1H-1,2,3,6-tetrahydropyrimidin-4-yl having a suitable substituent {such as $C_{1-4}$ alkyl (for example $CH_3$) or $C_{1-4}$ fluoroalkyl (for example $CF_3$, $CH_2CF_3$ or $C_2F_5$)} in the 3-position;

6-oxo-1H-1,6-dihydropyridin-3-yl having a suitable electron withdrawing substituent {such as $C_{1-4}$ fluoroalkyl (for example $CF_3$, $CH_2CF_3$ or $C_2F_5$) or cyano} in the 2-position or the 5-position and optionally substituted in other positions;

a $CO_2H$ group on an optionally substituted naphthyl ring; or, an $NHS(O)_2(C_{1-4}$ alkyl) (for example $NHS(O)_2CH_3$) group on an optionally substituted aromatic heterocyclyl ring (for example pyridinyl, pyrimidinyl or thiazolyl);

or, where possible, a tautomer thereof; the optional substituents being as defined above.

In yet another aspect the present invention provides a compound of formula (I) wherein $R^3$ is:

2-oxo-thiazol-5-yl having a suitable electron withdrawing substituent {such as $C_{1-4}$ fluoroalkyl (for example $CF_3$, $CH_2CF_3$ or $C_2F_5$), a phenyl group (for example 4-fluorophenyl) or a heterocyclyl group (for example pyridyl)} in the 4-position;

1H-1,2,3-triazol-4-yl having a suitable substituent {such as $C_{1-4}$ alkyl (for example $CH_3$ or $CH(CH_3)_2$), $C_{1-4}$ fluoroalkyl (for example $CF_3$, $CH_2CF_3$ or $C_2F_5$), S—$R^4$ (wherein $R^4$ is $C_{1-4}$ alkyl [for example $CH_3$] or $C_{1-4}$ fluoroalkyl [for example $CF_3$, $CH_2CF_3$ or $C_2F_5$]), $N(C_{1-4}$ alkyl)$S(O)_2(C_{1-4}$ alkyl) or a phenyl group (for example 4-fluorophenyl)} in the 5-position; or, 6-oxo-1H-1,6-dihydropyridin-3-yl having $C_{1-4}$ fluoroalkyl (for example $CF_3$, $CH_2CF_3$ or $C_2F_5$) or cyano in the 2-position or the 5-position.

In another aspect the present invention provides a compound of formula (I) wherein $R^3$ is:

2-oxo-thiazol-5-yl having $CF_3$ or $C_2F_5$ in the 4-position;

1H-1,2,3-triazol-4-yl having $CF_3$, $C_2F_5$, $SCF_3$, $SCH_2CF_3$ or $SC_2F_5$ (for example $CF_3$ or $SCH_2CF_3$) in the 5-position; or, 6-oxo-1H-1,6-dihydropyridin-3-yl having $CF_3$ or $C_2F_5$ in the 2-position.

In yet another aspect the present invention provides a compound of formula (I) wherein the 2-hydroxy group has the stereochemistry shown below:

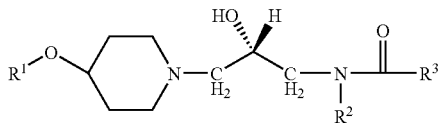
(I)

Compounds of the invention are illustrated in the Examples below.

Compounds of the present invention can be prepared by methods described, or analogous to those described, in the art (for example WO 03/068743). Intermediates for such processes can be prepared by methods described, or analogous to those described, in the art (for example WO 03/068743).

A compound of formula (I) can be prepared by reacting a compound of formula (II):

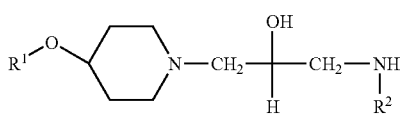
(II)

wherein $R^1$ and $R^2$ are as defined above, with a compound of formula (III):

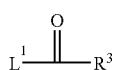
(III)

wherein $L^1$ is a leaving group (for example a hydroxy or chloro leaving group), and $R^3$ is as defined above; in the presence of a base (for example a tri($C_{1-6}$ alkyl)amine base (such as triethylamine or diisopropylethylamine) or N,N-dimethylformamide), in the presence of a suitable solvent (for example N,N-dimethylformamide, tetrahydrofuran, dichloromethane or dioxane, or a mixture of one or more of these solvents) optionally in the presence of a coupling agent (for example bromo-tris-pyrrolidinophosphonium hexafluorophosphate, PyBrOP or O-(7-azabenzotriazol-1-yl)-N,N,N',N'-tetramethyluronium hexafluorophosphate).

A compound of formula (II) can be prepared as described in WO 00/58305 or WO 01/77101, or by reacting a compound of formula (IV):

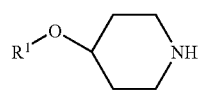
(IV)

wherein $R^1$ is defined above, with:
(i) a compound of formula (V):

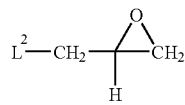
(V)

in which $L^2$ is a leaving group (for example chloro or nosyloxy {3-$NO_2$—$C_6H_4$—$S(O)_2O$—}) followed by reaction with ammonia, an amine $R^2$—$NH_2$ or with sodium azide and subsequent reduction with, for example, triphenylphosphine; or,
(ii) with a compound of formula (VI):

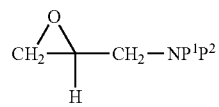
(VI)

in which $P^1$ and $P^2$ are, alone or together, suitable protective groups (for example together they form phthalimide), or either $P^1$ or $P^2$ is $R^2$, followed by deprotection using, for example when $P^1$ and $P^2$ form phthalimide, hydrazine.

A compound of formula (V) can be obtained commercially or can be prepared using methods described in the literature.

A compound of formula (VI) can be prepared by reacting (R) or (S) glycidol under Mitsunobu reaction conditions with, for example, phthalimide, 1,1-(azodicarbonyl)dipiperidine and tributylphosphine (*Tetrahedron Lett.* 1993, 34, 1639).

Further, a compound of formula (I) can be prepared by routine adaptation of: the routes described above, methods described in the art, or the Examples recited below. The intermediates identified above are commercially available or can be prepared by using or adapting methods described in the art.

In another aspect the present invention provides processes for the preparation of compounds of formula (I).

The compounds of the invention have activity as pharmaceuticals, in particular as modulators of chemokine receptor (for example CCR3) activity, and may be used in the treatment of autoimmune, inflammatory, proliferative or hyperproliferative diseases, or immunologically-mediated diseases (including rejection of transplanted organs or tissues and Acquired Immunodeficiency Syndrome (AIDS)).

In one aspect examples of these conditions are:
(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;

(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;
  (3) (skin and eyes) psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitides erythemas, cutaneous eosinophilias, uveitis, Alopecia areata or vernal conjunctivitis;
(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);
(5) (Allograft rejection) acute and chronic following, for example, transplantation of kidney, heart, liver, lung, bone marrow, skin or cornea; or chronic graft versus host disease; and/or
(6) (other tissues or diseases) Alzheimer's disease, multiple sclerosis, atherosclerosis, Acquired Immunodeficiency Syndrome (AIDS), Lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, Sezary syndrome, idiopathic thrombocytopenia pupura or disorders of the menstrual cycle.

The compounds of the invention are also H1 antagonists and may be used in the treatment of allergic disorders.

The compounds of the invention may also be used to control a sign and/or symptom of what is commonly referred to as a cold (for example a sign and/or symptom of a common cold or influenza or other associated respiratory virus infection).

According to a further feature of the invention there is provided a compound of formula (I), or a pharmaceutically acceptable salt thereof, for use in a method of treatment of a warm blooded animal (such as man) by therapy (including prophylaxis).

According to a further feature of the present invention there is provided a method for modulating chemokine receptor activity (for example CCR3 receptor activity), or antagonising H1, in a warm blooded animal, such as man, in need of such treatment, which comprises administering to said animal an effective amount of a compound of the formula (I), or a pharmaceutically acceptable salt thereof.

The invention also provides a compound of the formula (I), or a pharmaceutically acceptable salt thereof, for use as a medicament.

In another aspect the invention provides the use of a compound of formula (I), or a pharmaceutically acceptable salt thereof, in the manufacture of a medicament for use in therapy (for example modulating chemokine receptor activity (for example CCR3 receptor activity), or antagonising H1, in a warm blooded animal, such as man).

The invention further provides the use of a compound of formula (I), or a pharmaceutically acceptable salt thereof, in the manufacture of a medicament for use in the treatment of:
(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;
(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;
(3) (skin and eyes) psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitides erythemas, cutaneous eosinophilias, uveitis, Alopecia areata or vernal conjunctivitis;
(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);
(5) (Allograft rejection) acute and chronic following, for example, transplantation of kidney, heart, liver, lung, bone marrow, skin or cornea; or chronic graft versus host disease; and/or
(6) (other tissues or diseases) Alzheimer's disease, multiple sclerosis, atherosclerosis, Acquired Immunodeficiency Syndrome (AIDS), Lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, sezary syndrome, idiopathic thrombocytopenia pupura or disorders of the menstrual cycle;
in a warm blooded animal, such as man.

In a further aspect a compound of formula (I), or a pharmaceutically acceptable salt thereof, is useful in the treatment of asthma {such as bronchial, allergic, intrinsic, extrinsic or dust asthma, particularly chronic or inveterate asthma (for example late asthma or airways hyper-responsiveness)}; or rhinitis {including acute, allergic, atrophic or chronic rhinitis, such as rhinitis caseosa, hypertrophic rhinitis, rhinitis purulenta, rhinitis sicca or rhinitis medicamentosa; membranous rhinitis including croupous, fibrinous or pseudomembranous rhinitis or scrofulous rhinitis; seasonal rhinitis including rhinitis nervosa (hay fever) or vasomotor rhinitis}.

In a still further aspect a compound of formula (I), or a pharmaceutically acceptable salt thereof, is useful in the treatment of asthma.

The present invention also provides the use of a compound of formula (I), or a pharmaceutically acceptable salt thereof, in the manufacture of a medicament for use in the treatment of asthma or rhinitis.

The present invention further provides a method of treating a chemokine mediated disease state (for example a CCR3 mediated disease state, such as asthma) in a warm blooded animal, such as man, which comprises administering to a mammal in need of such treatment an effective amount of a compound of formula (I), or a pharmaceutically acceptable salt thereof.

In order to use a compound of the invention, or a pharmaceutically acceptable salt thereof, for the therapeutic treatment of a warm blooded animal, such as man, in particular modulating chemokine receptor (for example CCR3 receptor) activity or antagonising H1, said ingredient is normally formulated in accordance with standard pharmaceutical practice as a pharmaceutical composition.

Therefore in another aspect the present invention provides a pharmaceutical composition which comprises a compound of the formula (I), or a pharmaceutically acceptable salt thereof (active ingredient), and a pharmaceutically acceptable adjuvant, diluent or carrier. In a further aspect the present invention provides a process for the preparation of said composition which comprises mixing active ingredient with a pharmaceutically acceptable adjuvant, diluent or carrier. Depending on the mode of administration, the pharmaceutical composition will, for example, comprise from 0.05 to 99% w (per cent by weight), such as from 0.05 to 80% w, for example from 0.10 to 70% w, such as from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art into the form of, for example, aerosols, dry powder formulations, tablets, capsules, syrups, powders, granules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule which contains between 0.1 mg and 1 g of active ingredient.

In another aspect a pharmaceutical composition of the invention is one suitable for intravenous, subcutaneous or intramuscular injection.

Each patient may receive, for example, an intravenous, subcutaneous or intramuscular dose of 0.01 mgkg$^{-1}$ to 100 mgkg$^{-1}$ of the compound, for example in the range of 0.1 mgkg$^{-1}$ to 20 mgkg$^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

The invention further relates to combination therapies or compositions wherein a compound of formula (I), or a pharmaceutically acceptable salt thereof, or a pharmaceutical composition comprising a compound of formula (I), or a pharmaceutically acceptable salt thereof, is administered concurrently (possibly in the same composition) or sequentially with an agent for the treatment of any one of the above disease states.

In particular, for the treatment of the inflammatory diseases rheumatoid arthritis, psoriasis, inflammatory bowel disease, COPD, asthma and allergic rhinitis a compound of the invention can be combined with a TNF-α inhibitor (such as an anti-TNF monoclonal antibody (such as Remicade, CDP-870 and D.sub2.E.sub7.), or a TNF receptor immunoglobulin molecule (such as Enbrel.reg.)), a non-selective COX-1/COX-2 inhibitor (such as piroxicam or diclofenac; a propionic acid such as naproxen, flubiprofen, fenoprofen, ketoprofen or ibuprofen; a fenamate such as mefenamic acid, indomethacin, sulindac or apazone; a pyrazolone such as phenylbutazone; or a salicylate such as aspirin), a COX-2 inhibitor (such as meloxicam, celecoxib, rofecoxib, valdecoxib or etoricoxib) low dose methotrexate, lefunomide; ciclesonide; hydroxychloroquine, d-penicillamine or auranofin, or parenteral or oral gold.

The present invention still further relates to the combination of a compound of the invention together with:

a leukotriene biosynthesis inhibitor, a 5-lipoxygenase (5-LO) inhibitor or a 5-lipoxygenase activating protein (FLAP) antagonist, such as zileuton, ABT-761, fenleuton, tepoxalin, Abbott-79175, Abbott-85761, an N-(5-substituted)-thiophene-2-alkylsulfonamide, a 2,6-di-tert-butylphenol hydrazones, a methoxytetrahydropyran such as Zeneca ZD-2138, SB-210661, a pyridinyl-substituted 2-cyanonaphthalene compound such as L-739,010; a 2-cyanoquinoline compound such as L-746,530; an indole or quinoline compound such as MK-591, MK-886 or BAY×1005;

a receptor antagonist for a leukotriene LTB.sub4., LTC.sub4., LTD.sub4. or LTE.sub4. selected from the group consisting of a phenothiazin-3-one such as L-651,392; an amidino compound such as CGS-25019c; a benzoxalamine such as ontazolast; a benzenecarboximidamide such as BIIL 284/260; or a compound such as zafirlukast, ablukast, montelukast, pranlukast, verlukast (MK-679), RG-12525, Ro-245913, iralukast (CGP 45715A) or BAY×7195;

a PDE4 inhibitor including an inhibitor of the isoform PDE4D;

an antihistaminic H.sub1. receptor antagonist such as cetirizine, loratadine, desloratadine, fexofenadine, astemizole, azelastine or chlorpheniramine;

a gastroprotective H.sub2. receptor antagonist;

an α.sub1.- and α.sub2.-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride or ethylnorepinephrine hydrochloride;

an anticholinergic agent such as ipratropium bromide, tiotropium bromide, oxitropium bromide, pirenzepine or telenzepine;

a β.sub1.- to β.sub4.-adrenoceptor agonist such as metaproterenol, isoproterenol, isoprenaline, albuterol, salbutamol, formoterol, salmeterol, terbutaline, orciprenaline, bitolterol mesylate or pirbuterol, or a methylxanthanine including theophylline and aminophylline; sodium cromoglycate; or a muscarinic receptor (M1, M2, and M3) antagonist;

an insulin-like growth factor type I (IGF-1) mimetic;

an inhaled glucocorticoid with reduced systemic side effects, such as prednisone, prednisolone, flunisolide, triamcinolone acetonide, beclomethasone dipropionate, budesonide, fluticasone propionate or mometasone furoate;

an inhibitor of a matrix metalloprotease (MMP), such as a stromelysin, a collagenase, or a gelatinase or aggrecanase; such as collagenase-1 (MMP-1), collagenase-2 (MMP-8), collagenase-3 (MMP-13), stromelysin-1 (MMP-3), stromelysin-2 (MMP-10), and stromelysin-3 (MMP-11) or MMP-12;

a modulator of chemokine receptor function such as CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and CX$_3$CR1 for the C—X$_3$—C family;

an osteoporosis agent such as roloxifene, droloxifene, lasofoxifene or fosomax;

an immunosuppressant agent such as FK-506, rapamycin, cyclosporine, azathioprine or methotrexate;

a compound useful in the treatment of AIDS and/or HIV infection for example: an agent which prevents or inhibits the viral protein gp120 from engaging host cell CD4 {such as soluble CD4 (recombinant); an anti-CD4 antibody (or modified/recombinant antibody) for example PRO542; an anti-group120 antibody (or modified/recombinant antibody); or another agent which interferes with the binding of group120 to CD4 for example BMS806}; an agent which prevents binding to a chemokine receptor, other than CCR5, used by the HIV virus {such as a CXCR4 agonist or antagonist or an anti-CXCR4 antibody}; a compound which interferes in the fusion between the HIV viral envelope and a cell membrane {such as an anti-group 41 antibody; enfuvirtide (T-20) or T-1249}; an inhibitor of DC-SIGN (also known as CD209) {such as an anti-DC-SIGN antibody or an inhibitor of DC-SIGN binding}; a nucleoside/nucleotide analogue reverse transciptase inhibitor {for example zidovudine (AZT), nevirapine, didanosine (ddI), zalcitabine (ddC), stavudine (d4T), lamivudine (3TC), abacavir, adefovir or tenofovir (for example as free base or as disoproxil fumarate)}; a non-nucleoside reverse transciptase inhibitor {for example nevirapine, delavirdine or efavirenz}; a protease inhibitor {for example ritonavir, indinavir, saquinavir (for example as free base or as mesylate salt), nelfinavir (for example as free base or as mesylate salt), amprenavir, lopinavir or atazanavir (for example as free base or as sulphate salt)}; a ribonucleotide reductase inhinbitor {for example hydroxyurea}; or an antiretroviral {for example emtricitabine}; or, an existing therapeutic agent for the treatment of osteoarthritis, for example a non-steroidal anti-inflammatory agent (hereinafter NSAID's) such as piroxicam or diclofenac, a propionic acid such as naproxen, flubiprofen, fenoprofen, ketoprofen or ibuprofen, a fenamate such as mefenamic acid, indomethacin, sulindac or apazone, a pyrazolone such as phenylbutazone, a salicylate such as aspirin, a COX-2 inhibitor such as celecoxib, valdecoxib, rofecoxib or etoricoxib, an analgesic or intra-articular therapy such as a corticosteroid or a hyaluronic acid such as hyalgan or synvisc, or a P2X7 receptor antagonist.

The present invention still further relates to the combination of a compound of the invention together with: (i) a tryptase inhibitor; (ii) a platelet activating factor (PAF) antagonist; (iii) an interleukin converting enzyme (ICE) inhibitor; (iv) an IMPDH inhibitor; (v) an adhesion molecule inhibitor including a VLA-4 antagonist; (vi) a cathepsin; (vii) a MAP kinase inhibitor; (viii) a glucose-6 phosphate dehydrogenase inhibitor; (ix) a kinin-$B_1$- and $B_2$-receptor antagonist; (x) an anti-gout agent, e.g., colchicine; (xi) a xanthine oxidase inhibitor, e.g., allopurinol; (xii) an uricosuric agent, e.g., probenecid, sulfinpyrazone or benzbromarone; (xiii) a growth hormone secretagogue; (xiv) a transforming growth factor (TGFβ); (xv) a platelet-derived growth factor (PDGF); (xvi) a fibroblast growth factor, e.g., basic fibroblast growth factor (bFGF); (xvii) a granulocyte macrophage colony stimulating factor (GM-CSF); (xviii) a capsaicin cream; (xix) a Tachykinin $NK_1$. and $NK_3$. receptor antagonist selected from the group consisting of NKP-608C; SB-233412 (talnetant); and D-4418; (xx) an elastase inhibitors selected from the group consisting of UT-77 and ZD-0892; (xxi) a TNFα converting enzyme inhibitor (TACE); (xxii) an induced nitric oxide synthase inhibitor (iNOS); or (xxiii) a chemoattractant receptor-homologous molecule expressed on TH2 cells (a CRTH2 antagonist).

The pKa of a compound of formula (I) is measured using one of the following methodologies.

Method A

The apparatus used consists of a Sirius $GLpK_a$ instrument with DPAS (Dip Probe Absorption Spectroscopy) attachment. Key elements of the apparatus are a Sirius pH electrode, stirrer, titrant dispensing tubes, a multi-tipped dispenser, motor driven dispensing syringes, fibre optic UV probe and diode array detector. In addition, solutions in PTFE containers of ionic strength adjusted (0.10 M KCl) distilled water, nominally 0.50 M HCl, nominally 0.50 M KOH and 80% v/v methanol:water are also housed within the instrument. The titration solutions are constantly purged with oxygen free nitrogen. The reservoir for the potassium hydroxide solution is further protected from atmospheric contamination by a soda-lime guard-tube. Samples are placed in titration vessels which in turn are placed in a movable autosampler tray (maximum capacity 48 samples). The electrode, stirrer, dispensing tubing/tips and DPAS probe are housed on a movable, automated z-tower unit, which, controlled by software, positions itself in the appropriate titration vessel when titrating. The Sirius $GLpK_a$ instrument is directly connected to a dedicated PC supporting software for assay setup and subsequent data analysis. Assays are set up using the GlpKaControl software and results are analysed using the pKaLOGP and pKaUV software on the PC. The software also allows determination of multiple $pK_a$s using complex curve fitting analyses.

Method B: Potentiometric Method

Two types of potentiometric titrations may be performed in order to determine a compound's $pK_a/pK_a$s; a purely aqueous titration (recommended for fairly water soluble compounds) and a cosolvent titration, where variable amounts of methanol are added to the sample in addition to ionic strength adjusted water (recommended for compounds which are not soluble in water). For the latter, a value for the compound's $pK_a$ in pure ionic strength adjusted water can be estimated by the Yasuda-Shedlovsky procedure. This involves measuring the apparent $pK_a$ of the compound at three known weight percentages of methanol:water (transposed into reciprocals of the dielectric constants of the medium, $1/\epsilon_r$) and then extrapolating to 0 wt % methanol ($1/\epsilon_r = 1.282 \times 10^{-3}$).

The $GLpK_a$ instrument unit also houses two aqueous wash containers (containing distilled water), a waste beaker (to dispense extraneous solutions into) and a container holding pH 7.00 buffer solution for the electrode to be immersed in during periods between titrations. Each time a set of titrations is carried out, these solutions are replaced. Position 1 in the autosampler contains a titration vessel containing pH 7.00 buffer solution (changed for each titration set). For each titration set to be run, position 2 houses a titration vessel into which ionic strength adjusted water is dispensed (typically 15.00 mL). This in turn is adjusted to pH 1.80 with aqueous HCl and then titrated to pH 12.20 by gradual addition of aqueous KOH. This is referred to as a blank titration and is employed by the pKaLogP software in order to calibrate the pH electrode and to standardise the HCl solution, using the so-called four-plus parameter procedure. Periodically, (typically every 3 months, or when the titration solutions run low) the titration solutions are replaced and the KOH solution standardised against potassium hydrogen phthalate using a standardisation procedure within the GLpKaControl software. Between 1-2 mg of each sample must be accurately weighed out. Samples are placed in provided glass titration vessels. The weight of compound must be entered into the GLpKaControl software. Other parameters that need to be entered are; the molecular weight of the compound, assay type (aqueous, cosolvent), number of assays in the beaker (1 for aqueous titrations, 3 for cosolvent/mixed solvent titrations), formula (eg. X for a compound not present as a salt, or XHCl for a compound introduced as a hydrochloride salt), expected number of $pK_a$s (from known structure), minimum pH (1.80 for operational minimum of electrode), maximum pH (12.20 for operational maximum of electrode), first assay direction (low to high pH recommended for bases, high to low pH recommended for acids), starting aqueous phase volume (minimum 8.00 mL, typically 15.00 mL for purely aqueous titrations and 9.00 mL for mixed solvent titrations), and pH step between points ($\Delta$pH=0.10 units recommended). If mixed solvent titrations are carried out on a compound, then additional information needs to be entered; assay direction for second and third titrations (see first assay direction), and additional water volume for second and third assays (automatically calculated when using the cosolvent weight percentage tool).

A number of samples (maximum 48) are placed in the autosampler and the pertinent information for each titration (weight of compound, molecular weight etc.) downloaded to the $GLpK_a$ instrument from the dedicated PC. The "run assays" option on the $GLpK_a$ instrument is selected and the titration run proceeds. At the end of the run, the titration data is uploaded to the PC and analysed using the pKaLOGP software. The first sample to be analysed is the blank titration. Curve fitting procedures are used to fit the measured data to a theoretical curve allowing the derivation of the exact concentration of the HCl solution, and also the values of various parameters (four-plus parameters) which characterise the behaviour of the electrode as a function of pH. These data are then used in the subsequent analysis of the other samples. The rest of the samples are analysed using further curve fitting procedures that extract the pKas of the compound by fitting the observed data to a theoretical curve. For cosolvent titrations the observed pKas from each sample at different percentages of methanol are analysed using the Yasuda-Shedlovsky procedure in the pKaLOGP software which extraplotes the observed pKas to the true pKas in 100% aqueous solution.

Method C: DPAS (Dip Probe Absorption Spectroscopy) Method

This method determines pKas by measuring UV spectra of a compound as a function of pH. This method is most suitable for compounds where the ionising centre is situated close to an aromatic or conjugated system within the molecule such that a change in the extent of ionisation will lead to a change in the UV spectrum. Due to the good sensitivity of UV spectroscopy, this method is suitable for rather insoluble compounds.

This method requires a blank titration to be run in just the same way as the potentiometric method. However, for the samples, two vials are required for each sample. Into one vial is placed a small amount of a DMSO solution of the compound (typically 50 μl of a 1.5 mM solution) along with some phosphate buffer to give some pH stability during the titration (typically 100 μL of an aqueous solution prepared from 0.2 g potassium dihydrogen orthophosphate and 100 mL 0.1 M KCl solution). The titrator will then add water (typically 10 mL) to this solution and then carry out a pH titration while collecting UV spectra at each pH. The second vial should contain and equivalent volume of neat DMSO and an equivalent volume of phosphate buffer. The titrator will then add an equivalent volume of water to this solution and take a UV spectrum of it to act as a reference (this is actually done before the pH titration of the corresponding sample solution).

Again the first sample to be analysed is the blank titration which allows determination of the exact HCl concentration and the values of four-plus parameters. The pKaUV software is then used to extract the pKas of the compound from the 3 dimensional data (absorbance, wavelength, pH) that was collected during the titration. The software uses a complex algorithm (target factor analysis) to extract the UV spectrum of each protonation state of the molecule as well as each pKa of the molecule from the raw 3 dimensional data.

The invention will now be illustrated by the following non-limiting Examples in which, unless stated otherwise:

(i) when given, $^1$H NMR data is quoted and is in the form of delta values for major diagnostic protons, given in parts per million (ppm) relative to tetramethylsilane (TMS) as an internal standard, determined at 300 MHz or 400 MHz using perdeuterio DMSO-D6 ($CD_3SOCD_3$), methanol-D4 ($CD_3OD$) or $CDCl_3$ as the solvent unless otherwise stated;

(ii) mass spectra (MS) were run with an electron energy of 70 electron volts in the chemical ionisation (CI) mode using a direct exposure probe; where indicated ionisation was effected by electron impact (EI) or fast atom bombardment (FAB) or electrospray (ESI); where values for m/z are given, generally only ions which indicate the parent mass are reported, and unless otherwise stated the mass ion quoted is the positive mass ion—$(M+H)^+$;

(iii) the title and subtitle compounds of the examples and methods were named using the ACD/Index name program version 4.55 from Advanced Chemistry Development, Inc;

(iv) unless stated otherwise, reverse phase HPLC was conducted using a Symmetry, NovaPak or Xterra reverse phase silica column; and (v) the following abbreviations are used:

| | |
|---|---|
| DMF | N,N-Dimethylformamide |
| HPLC | High pressure liquid chromatography |
| RPHPLC | Reverse phase high pressure liquid chromatography |
| HATU | O-(7-Benzotriazol-1-N,N,N',N'-tetramethyluronium hexafluorophosphate |
| THF | Tetrahydrofuran |
| DCM | Dichloromethane |
| d | Day(s) |
| h | Hour(s) |
| min | Minute(s) |

Preparation 1

(2R)-1-Amino-3-[4-(3,4-dichlorophenoxy)piperidin-1-yl]propan-2-ol

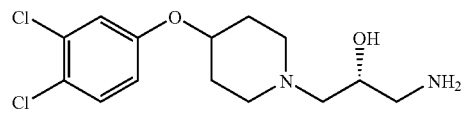

Step 1: 4-(3,4-Dichlorophenoxy)piperidine

4-Hydroxypiperidine (50 g) was added portionwise to a stirred suspension of potassium tert-butoxide (110.9 g) in THF (900 mL) at room temperature and under nitrogen. The mixture was heated at reflux and 1,2-dichloro-4-fluorobenzene (98 g) added dropwise over 30 min. The mixture was stirred at reflux for another 1 h then cooled down to room temperature, diluted with ethyl acetate (500 mL) and washed with water (500 mL). The organic phase was diluted further with ethyl acetate (500 mL) and extracted with 1M hydrochloric acid (200 mL). The aqueous extract was adjusted to over pH 10 by addition of a solution of sodium hydroxide and extracted twice with tert-butylmethyl ether (750 mL). The organic extracts were dried over magnesium sulfate, filtered and concentrated under vacuum to yield the sub-title compound as a dark oil which was used as such in the next step.

MS (ESI+ve) 246/248 [M+H]+

$^1$H NMR δ (CDCl$_3$) 1.60-1.70 (2H, m), 1.97-2.03 (2H, m), 2.75 (2H, td), 3.15 (2H, dt), 4.29-4.37 (1H, m), 6.78 (1H, dd), 7.00 (1H, d), 7.31 (1H, d).

Step 2: (2S)-1-Azido-3-[4-(3,4-dichlorophenoxy) piperidin-1-yl]propan-2-ol (2R)-Oxiran-2-ylmethyl 3-nitrobenzenesulfonate (21.1 g) in DMF (300 mL) was treated with triethylamine (22.6 mL) followed by 4-(3,4-dichlorophenoxy)-piperidine (20 g). The mixture was stirred overnight at 60° C. Sodium azide (16 g) was added to the mixture and the reaction was stirred for a further 72 h. The solution was carefully concentrated under vacuum and the residue was diluted with water (600 mL), extracted with ethyl acetate (1500 mL). The organic layer was washed twice with water (500 mL), then brine (200 mL) and concentrated under vacuum to afford an oil.

Step 3: (2R)-1-Amino-3-[4-(3,4-dichlorophenoxy) piperidin-1-yl]propan-2-ol

The oil from Step 2 was dissolved in wet tetrahydrofuran (225 mL) and was treated with triphenylphosphine (53.3 g). The reaction was heated at 60° C. and stirred for 4 h. The solvent was removed under vacuum, the residue redissolved into 2N hydrochloric acid (1 L) and the aqueous layer was extracted with ethyl acetate (3×700 mL). The aqueous phase was basified with aqueous 2 N sodium hydroxide solution and extracted with DCM (3×1 L). The combined organic layers were washed with brine, dried over sodium sulfate, filtered and concentrated under vacuum. The crude material was purified by chromatography (8% 7N ammonia in methanol/DCM) to give the title compound as a yellow oil (17 g).

MS (APCI+ve) 319/321 [M+H]+

$^1$H NMR δ (CDCl$_3$) 1.90-1.72 (2H, m), 2.06-1.91 (2H, m), 2.46-2.21 (3H, m), 2.60-2.49 (1H, m), 2.65 (1H, d), 2.72-2.61 (1H, m), 2.82 (1H, d), 2.94-2.84 (1H, m), 3.74-3.62 (1H, m), 4.0 (1H, app. sept.), 6.75 (1H, dd), 7.00 (1H, d), 7.31 (1H, d).

Preparation 2

(2R)-1-Amino-3-[4-(2,4-dichloro-3-methylphenoxy) piperidin-1-yl]propan-2-ol

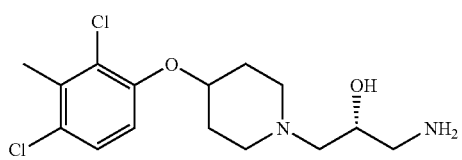

Prepared as described in Preparation 1 using 4-(2,4-dichloro-3-methylphenoxy)-piperidine.

MS (APCI+ve) 333/335 [M+H]+

$^1$H NMR δ (CD$_3$OD) 1.92-1.75 (2H, m), 2.08-1.90 (2H, m), 2.72-2.57 (1H, m), 2.93-2.72 (4H, m), 3.35-3.24 (2H, m), 3.88-3.71 (1H, m), 4.54-4.37 (1H, m), 6.94 (2H, d), 7.25 (2H, d).

Preparation 3

(R)-1-[4-(3,4-Dichlorophenoxy)piperidin-1-yl]-3-methylamino-propan-2-ol

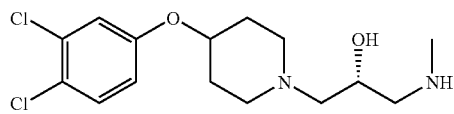

A solution of 4-(3,4-dichlorophenoxy)-1-[(2R)-oxiran-2-ylmethyl]piperidine (1.0 g), prepared as described in Preparation 1, Step 2 and concentrated from DMF, and methylamine (2.56 mL 40% v/v aqueous) in ethanol (15 mL) was heated at 60° C. in a sealed vessel for 16 h. The solvent was evaporated at reduced pressure and the residue was purified by flash column chromatography eluting with 8% 7M methanolic ammonia in DCM to give the title compound (0.875 g).

MS (APCI+ve) 333/335 [M+H]+

$^1$H NMR δ (CDCl$_3$) 2.38-2.27 (3H, m), 2.46 (3H, s), 2.48-2.42 (2H, m), 2.54 (1H, dd), 2.56-2.51 (2H, m), 2.65 (1H, dd), 2.71-2.65 (2H, m), 2.91-2.86 (1H, m), 3.86-3.80 (1H, m), 4.32-4.26 (1H, m), 6.75 (1H, dd), 6.99 (1H, d), 7.31 (1H, d).

Preparation 4

(R)-1-[4-(2,4-Dichloro-3-methylphenoxy)piperidin-1-yl]-3-(methylamino)propan-2-ol

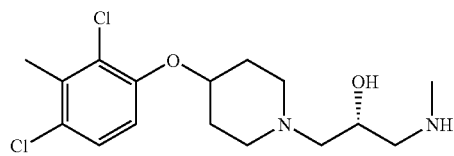

Prepared as described in Preparation 2 and 3 from 4-(2,4-dichloro-3-methylphenoxy)piperidine to give the title compound.

$^1$H NMR δ(CDCl$_3$) 1.58-2.00 (4H, m), 2.28-2.71 (10H, m), 2.46 (3H, s), 2.87-2.95 (1H, m), 3.49 (1H, s), 3.82-3.88 (1H, m), 4.33-4.39 (1H, m), 6.75 (1H, d), 7.19 (1H, d).

EXAMPLE 1

N-{(2R)-3-[4-(3,4-Dichlorophenoxy)piperidin-1-yl]-2-hydroxypropyl}-6-oxo-2-(trifluoromethyl)-1,6-dihydropyridine-3-carboxamide

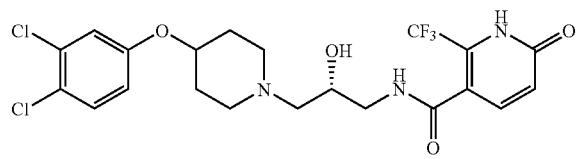

6-Oxo-2-(trifluoromethyl)-1,6-dihydropyridine-3-carboxylic acid (*Organic Process Research and Development* 1997, 1, 370-378; 0.50 g) was dissolved in thionyl chloride (10 mL) and heated at reflux for 3 h. The solvent was evaporated and the residue was azeotroped with toluene (10 mL). The resultant pale yellow solid was dissolved in ethyl acetate (10 mL) and added dropwise to a solution of (2R)-1-amino-3-[4-(3,4-dichlorophenoxy)piperidin-1-yl]propan-2-ol (0.770 g) and triethylamine (1.68 mL) in DCM (25 mL). The mixture was stirred at room temperature for 18 h and the solvents were evaporated. The residue was dissolved in methanol (20 mL) and heated at reflux for 18 h. The solvents were evaporated and purification by RPHPLC (Novapak, 0.1% ammonium acetate/acetonitrile) afforded the title compound as a colourless solid (0.520 g).

The title compound has pKa 5.9 (measured using method B), and pKa 6.3 (calculated by ACD).

MS (APCI+ve) 508/510 [M+H]$^+$ $^1$H NMR δ (CD$_3$OD) 1.89-1.78 (2H, m), 2.10-1.99 (2H, m), 2.65-2.51 (4H, m), 2.99-2.87 (2H, m), 3.40-3.34 (1H, m), 3.48 (1H, dd), 4.04-3.96 (1H, m), 4.50-4.42 (1H, m), 6.84 (1H, d), 6.92 (1H, ddd), 7.14 (1H, dd), 7.41 (1H, dd), 7.75 (1H, d).

EXAMPLE 2

N-{(2R)-3-[4-(2,4-Dichloro-3-methylphenoxy)piperidin-1-yl]-2-hydroxypropyl}-6-oxo-2-(trifluoromethyl)-1,6-dihydropyridine-3-carboxamide

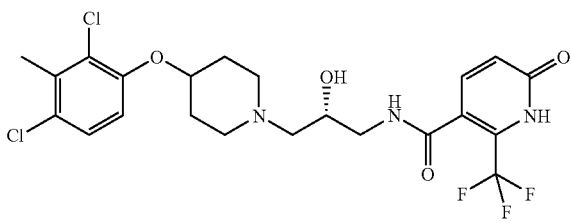

6-Oxo-2-(trifluoromethyl)-1,6-dihydropyridine-3-carboxylic acid (0.100 g) was dissolved in thionyl chloride (2 mL) and heated at reflux for 3 h. The solvent was evaporated and the residue was azeotroped with toluene (5 mL). The resultant pale yellow solid was dissolved in tetrahydrofuran (2 mL) and added dropwise to a solution of (2R)-1-amino-3-[4-(2,4-dichloro-3-methylphenoxy)piperidin-1-yl]propan-2-ol (0.161 g, and triethylamine (0.337 mL) in DCM (5 mL). The mixture was stirred at room temperature for 18 h and the solvents were evaporated. The residue was dissolved in methanol (10 mL) and heated at reflux for 3 h. The solvents were evaporated and purification by RPHPLC (Symmetry, 0.1% ammonium acetate/acetonitrile) afforded the title compound as a colourless solid (0.520 g).

The title compound has pKa 6.3 (calculated using ACD).

MS (APCI+ve) 522/524 [M+H]$^+$ $^1$H NMR δ (CD$_3$OD) 1.97-2.23 (4H, m), 2.48 (3H, s), 2.81-3.07 (4H, m), 3.12-3.24 (2H, m), 3.31-3.52 (2H, m), 4.08-4.18 (1H, m), 4.62-4.69 (1H, m), 6.89 (1H, d), 7.02 (1H, d), 7.31 (1H, d), 7.80 (1H, d).

EXAMPLE 3

5-Bromo-N-{(2R)-3-[4-(3,4-dichlorophenoxy)piperidin-1-yl]-2-hydroxypropyl}-6-oxo-2-(trifluoromethyl)-1,6-dihydropyridine-3-carboxamide

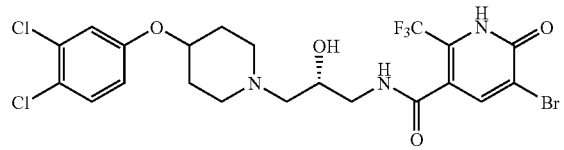

Step 1: Ethyl 5-bromo-6-oxo-2-(trifluoromethyl)-1,6-dihydropyridine-3-carboxylate To a solution of ethyl 6-oxo-2-(trifluoromethyl)-1,6-dihydropyridine-3-carboxylate (*Organic Process Research and Development* 1997, 1, 370-378; 0.10 g) in carbon tetrachloride was added N-bromosuccinimide (0.083 g). The mixture was heated at 80° C. for 24 h. Evaporation and the purification by flash column chromatography gave the subtitle compound as a colourless solid (0.10 g).

MS (ES−ve) 311/313 [M−H]$^-$ $^1$H NMR δ (CDCl$_3$) 1.38 (3H, t), 4.39 (2H, q), 8.34 (1H, s)

Step 2: 5-Bromo-6-oxo-2-(trifluoromethyl)-1,6-dihydropyridine-3-carboxylic acid

Ethyl 5-bromo-6-oxo-2-(trifluoromethyl)-1,6-dihydropyridine-3-carboxylate (0.25 g) was suspended in 30% aqueous hydrochloric acid and heated at reflux for 4 days. Cooling and filtration gave the subtitle compound (0.210 g).

$^1$H NMR δ (DMSO-d$_6$) 8.40 (1H, s), 13.40 (1H, s), 13.70 (1H, s).

Step 3: 5-Bromo-N-{(2R)-3-[4-(3,4-dichlorophenoxy)piperidin-1-yl]-2-hydroxypropyl}-6-oxo-2-(trifluoromethyl)-1,6-dihydropyridine-3-carboxamide Made by the method of Example 1 using 5-bromo-6-oxo-2-(trifluoromethyl)-1,6-dihydropyridine-3-carboxylic acid (0.10 g), thionyl chloride (2 mL), (2R)-1-amino-3-[4-(3,4-dichlorophenoxy)piperidin-1-yl]propan-2-ol (0.112 g) and triethylamine (0.244 mL) to yield the title compound as a colourless solid (0.096 g).

The title compound has pKa 4.5 (calculated using ACD).

MS (APCI−ve) 586 [M−H]$^-$ $^1$H NMR δ (CD$_3$OD) 1.99-2.13 (2H, m), 2.14-2.28 (2H, m), 2.97-3.28 (4H, m), 3.30-3.50 (4H, m), 4.13-4.22 (1H, m), 4.63-4.70 (1H, m), 6.98 (1H, dd), 7.22 (1H, d), 7.44 (1H, d), 7.88 (1H, s).

EXAMPLE 4

N-{(2R)-3-[4-(3,4-Dichlorophenoxy)piperidin-1-yl]-2-hydroxypropyl}-2,3-dihydro-2-oxo-4-(trifluoromethyl)-5-thiazolecarboxamide

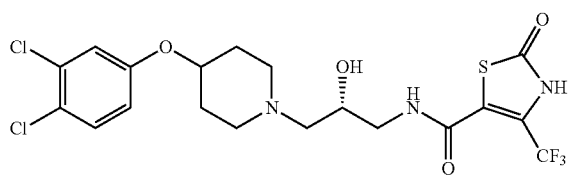

Step 1: 2,3-Dihydro-2-oxo-4-(trifluoromethyl)-5-thiazolecarboxylic acid

To a solution of ethyl 2,3-dihydro-2-oxo-4-(trifluoromethyl)-5-thiazolecarboxylic acid (Bionet Research, 2.0 g) in THF (20 mL) was added a solution of lithium hydroxide (0.696 g) in water (20 mL). The mixture was stirred at 50° C. for 72 h, cooled to room temperature and filtered. The filtrate was washed with ethyl acetate (10 mL), acidified to pH 3 using dilute hydrochloric acid and extracted with ethyl acetate (2×25 mL). The combined organic extractions were washed with water (2×50 mL), saturated brine solution, dried ($Na_2SO_4$), filtered and concentrated in vacuo to give the subtitle compound as a colourless solid (1.583 g).

MS (APCI–ve) 212 [M–H]$^-$
$^{13}$C NMR δ (CDCl$_3$) 171.3 (s), 161.1 (s), 129.8 (q, 39.8 Hz), 122.3 (q, 272.4 Hz), 115.1 (q, 3.0 Hz).

Step 2: N-{(2R)-3-[4-(3,4-Dichlorophenoxy)piperidin-1-yl]-2-hydroxypropyl}-2,3-dihydro-2-oxo-4-(trifluoromethyl)-5-thiazolecarboxamide Prepared as in Example 1 using 2,3-dihydro-2-oxo-4-(trifluoromethyl)-5-thiazolecarboxylic acid to afford the title compound as a cream foam (0.183 g).

The title compound has a pKa 4.7 (measured using Method B).

MS (APCI–ve) 512/514 [M–H)]$^-$
$^1$H NMR δ (CD$_3$OD) 2.06-1.94 (2H, m), 2.22-2.08 (2H, m), 3.00-2.86 (2H, ddd), 3.14-3.00 (2H, m), 3.30-3.18 (2H, m), 3.42-3.32 (2H, ddd), 4.11-4.03 (1H, m), 4.64-4.56 (1H, m), 6.94 (1H, dd), 7.18 (1H, d), 7.41 (1H, d).

EXAMPLE 5

N-{(2S)-3-[4-(3,4-Dichlorophenoxy)piperidin-1-yl]-2-hydroxypropyl}-N-methyl-2-oxo-4-(trifluoromethyl)-2,3-dihydro-1,3-thiazole-5-carboxamide

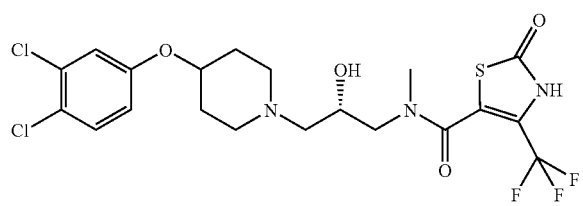

Prepared as Example 1 using (2R)-1-[4-(3,4-dichlorophenoxy)piperidin-1-yl]-3-(methylamino)propan-2-ol (150mg, 0.45 mmol) and 2-oxo-4-(trifluoromethyl)-2,3-dihydro-1,3-thiazole-5-carboxylic acid (0.096 g) to yield the title compound as a colourless solid (0.085 g).

The title compound has pKa 6.27 (calculated using ACD).
MS (APCI+ve) 528/530 [M+H]$^+$
$^1$H NMR δ (DMSO-d$_6$, 90° C.) 1.79-1.62 (2H, m), 2.03-1.88 (2H, m), 2.62-2.45 (2H, m), 2.93-2.82 (4H, m), 3.00 (3H, s), 3.24 (1H, dd), 3.52 (1H, dd), 3.91 (1H, quintet), 4.45 (1H, septet), 6.96 (1H, dd), 7.20 (1H, d), 7.46 (1H, d).

EXAMPLE 6

N-{(2S)-3-[4-(2,4-Dichloro-3-methylphenoxy)piperidin-1-yl]-2-hydroxypropyl}-N-methyl-2-oxo-4-(trifluoromethyl)-2,3-dihydro-1,3-thiazole-5-carboxamide

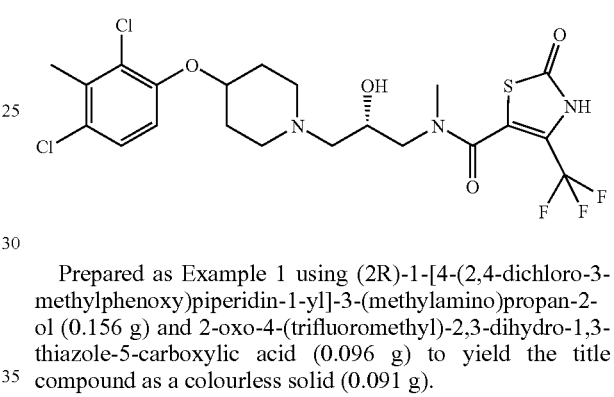

Prepared as Example 1 using (2R)-1-[4-(2,4-dichloro-3-methylphenoxy)piperidin-1-yl]-3-(methylamino)propan-2-ol (0.156 g) and 2-oxo-4-(trifluoromethyl)-2,3-dihydro-1,3-thiazole-5-carboxylic acid (0.096 g) to yield the title compound as a colourless solid (0.091 g).

The title compound has pKa 6.3 (calculated using ACD).
MS (APCI+ve) 542/544 [M+H]$^+$
$^1$H NMR δ (DMSO-d$_6$, 90° C.) 1.83-1.67 (2H, m), 2.01-1.87 (2H, m), 2.41 (3H, s), 2.61-2.50 (2H, m), 2.93-2.78 (4H, m), 2.99 (3H, s), 3.24 (1H, dd), 3.52 (1H, dd), 3.91 (1H, quintet), 4.47 (1H, septet), 7.05 (1H, d), 7.31 (1H, d).

EXAMPLE 7

N-{(2R)-3-[4-(3,4-Dichlorophenoxy)piperidin-1-yl]-2-hydroxypropyl}-2-oxo-4-(pentafluoroethyl)-2,3-dihydro-1,3-thiazole-5-carboxamide

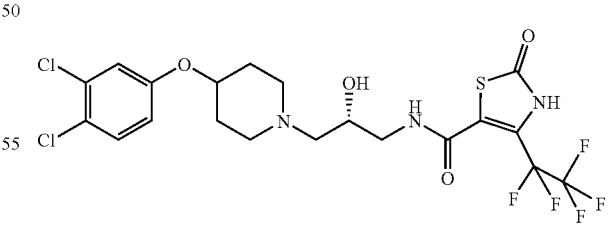

Step 1: 2-Oxo-4-(pentafluoroethyl)-2,3-dihydro-1,3-thiazole-5-carboxylic acid Ethyl 2-oxo-4-pentafluoroethyl)-2,3-dihydro-1,3-thiazole-5-carboxylate (*J. Het. Chem.* 22 1985 1621-1630; 0.240 g) in THF (6 mL) was treated with lithium hydroxide (0.120 g) in water (5 mL) and the mixture was heated at 50° C. for 4 d. The mixture was filtered and the residue was washed with water. The filtrate was washed with ethyl acetate. The aqueous layer was acidified with dilute hydrochloric acid and then extracted with ethyl acetate (3×50 mL). The organic extracts were washed with water and brine and then dried over sodium sulphate, filtered and evaporated to yield the subtitle compound as a solid (0.13 g).

Step 2: N-{(2R)-3-[4-(3,4-Dichlorophenoxy)piperidin-1-yl]-2-hydroxypropyl}-2-oxo-4-(pentafluoroethyl)-2,3-dihydro-1,3-thiazole-5-carboxamide Prepared as Example 1 using (2R)-1-amino-3-[4-(3,4-dichlorophenoxy)piperidin-1-yl]propan-2-ol (0.158 g) and 2-oxo-4-(pentafluoroethyl)-2,3-dihydro-1,3-thiazole-5-carboxylic acid (0.130 g) to yield the title compound as a colourless solid (0.074 g).

The title compound has pKa 6.1 (calculated using ACD).
MS (APCI+ve) 564/566 [M+H]$^+$
$^1$H NMR δ (DMSO-d$_6$) 1.86-1.72 (2H, m), 2.08-1.96 (2H, m), 2.84-2.59 (4H, m), 3.10-2.90 (1H, m,obscured), 3.28-3.16 (3H, m), 3.85 (1H, quintet), 4.53 (1H, septet), 6.98 (1H, dd), 7.23 (1H, d), 7.47 (1H, d), 7.48 (1H, s).

EXAMPLE 8

N-{(2R)-3-[4-(3,4-Dichlorophenoxy)piperidin-1-yl]-2-hydroxypropyl}-5-methyl-1H-1,2,3-triazole-4-carboxamide

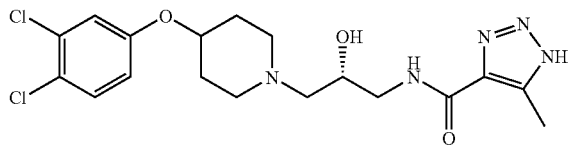

Prepared as Example 1 using 5-methyl-1H-1,2,3-triazole-4-carboxylic acid (*Berichte* 1963 96, 802-812; 0.060 g) to yield the title compound as a colourless solid (0.063 mg).

The title compound has pKa 7.5 (measured using Method B), and pKa 7.5 (calculated using ACD).
MS (APCI+ve) 428/430[M+H]$^+$
$^1$H NMR δ (DMSO-d$_6$) 1.73-1.60 (2H, m), 1.97-1.86 (2H, m), 2.41-2.28 (4H, m), 2.45 (3H, s), 2.79-2.67 (2H, m), 3.43-3.24 (2H, m), 3.78 (1H, quintet), 4.39 (1H, septet), 6.95 (1H, dd), 7.18 (1H, d), 7.44 (1H,d), 7.90 (1H, t),

EXAMPLE 9

N-{(2R)-3-[4-(2,4-Dichloro-3-methylphenoxy)piperidin-1-yl]-2-hydroxypropyl}-5-methyl-1H-1,2,3-triazole-4-carboxamide

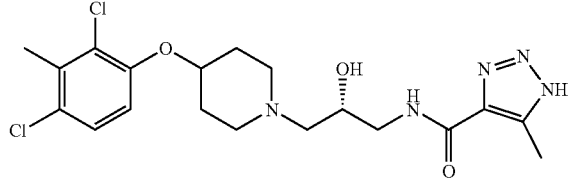

Prepared as Example 1 using (2R)-1-amino-3-[4-(2,4-dichloro-3-methylphenoxy)piperidin-1-yl]propan-2-ol (0.158 g) and 5-methyl-1H-1,2,3-triazole-4-carboxylic acid to yield the title compound as a colourless solid (0.037 g).

The title compound has pKa 7.5 (calculated using ACD).
MS (APCI+ve) 442/444 [M+H]$^+$ $^1$H NMR δ (DMSO-d$_6$, 90° C.) 1.78-1.65 (2H, m), 1.97-1.86 (2H, m), 2.43-2.32 (4H, m), 2.41 (3H, s), 2.45 (3H, s), 2.79-2.67 (2H, m), 3.28 (1H, dt), 3.40 (1H, dt), 3.78 (1H, quintet), 4.43 (1H, septet), 7.03 (1H, d), 7.30 (1H, d), 7.89 (1H, t).

EXAMPLE 10

5-Cyano-N-{(2R)-3-[4-(3,4-dichlorophenoxy)piperidin-1-yl]-2-hydroxypropyl}-6-oxo-2-(trifluoromethyl)-1,6-dihydropyridine-3-carboxamide

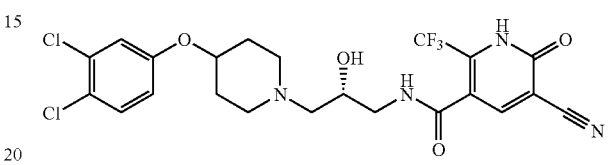

5-Cyano-6-oxo-2-(trifluoromethyl)-1,6-dihydropyridine-3-carboxylic acid (*Farmaco* 1997, 52(5), 331-337; 0.115 g) was dissolved in thionyl chloride (3 mL) and heated at reflux for 2 h. The solvent was evaporated and the residue was azeotroped with toluene (10 mL). The resultant solid was dissolved in THF (5 mL) and added dropwise to a solution of (2R)-1-[4-(3,4-dichlorophenoxy)-piperidin-1-yl]-3-methylamino-propan-2-ol (0.150 g) and triethylamine (0.3 mL) in DCM (5 mL). The mixture was stirred at room temperature for 18 h and the solvents were evaporated. Purification by RPHPLC (Novapak, 0.1% ammonium acetate/acetonitrile) and normal phase chromatography (NH$_3$/methanol/DCM) afforded the title compound as a colourless solid (0.123 g).

The title compound has a pKa 3.4 (calculated using ACD).
MS (APCI+ve) 533/535 [M+H]$^+$
$^1$H NMR δ (CD$_3$OD) 2.13-1.99 (2H, m), 2.28-2.13 (2H, m), 3.10 (2H, dt), 3.34-3.14(2H, m), 3.50-3.36(4H, m), 4.21-4.12 (1H, m), 4.71-4.63 (1H, m), 6.96 (1H, dd), 7.21 (1H, d), 7.42 (1H, d), 7.85 (1H, s).

EXAMPLE 11

5-Cyano-N-{(2R)-3-[4-(2,4-dichloro-3-methylphenoxy)piperidin-1-yl]-2-hydroxypropyl}-6-oxo-2-(trifluoromethyl)-1,6-dihydropyridine-3-carboxamide

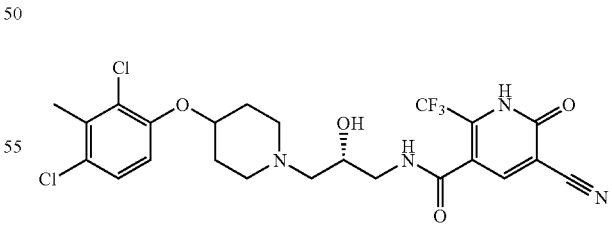

Prepared as Example 1 using (2R)-1-amino-3-[4-(2,4-dichloro-3-methylphenoxy)piperidin-1-yl]propan-2-ol to yield the title compound as a colourless solid (0.121 g).

The title compound has a pKa 3.0 (measured using Method B), and pKa 3.4 (calculated using ACD).
MS (APCI+ve) 547/549 [M+H]$^+$
$^1$H NMR δ (DMSO-d$_6$+ND$_4$OD) 1.72-1.61 (2H, m), 1.93-1.84 (2H, m), 2.37-2.24 (4H, m), 2.40 (3H, s), 2.72-2.63 (2H, m), 3.07 (1H, dd), 3.23 (1H, dd), 3.71 (1H, quintet), 4.48 (1H, septet), 7.10 (1H, d), 7.34 (1H, d), 7.66 (1H, s).

EXAMPLE 12

5-Cyano-N-{(2R)-3-[4-(3,4-dichlorophenoxy)piperidin-1-yl]-2-hydroxypropyl}-6-oxo-2-phenyl-1,6-dihydropyridine-3-carboxamide

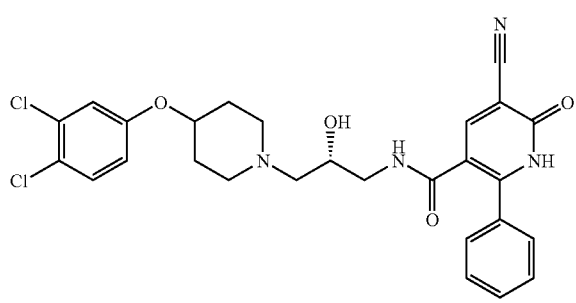

5-Cyano-6-oxo-2-phenyl-1,6-dihydropyridine-3-carboxylic acid (*European Journal of Medicinal Chemistry* 24(5), 517-519, 1989; 0.112 g) was dissolved in thionyl chloride (4 mL) and heated under reflux for 2 h. The solvent was removed in vacuo and the residue was azeotroped with toluene (10 mL). The resultant pale yellow solid was dissolved in THF (4 mL) and added dropwise to a solution of (2R)-1-amino-3-[4-(3,4-dichlorophenoxy)piperidin-1-yl]propan-2-ol (0.150 g) and triethylamine (0.7 mL) in DCM (2 mL). The mixture was stirred at room temperature overnight and the volatiles were removed in vacuo. The residue was dissolved in acetonitrile (6 mL) and purification by RPHPLC (Novapak, 0.1% ammonium acetate/acetonitrile) afforded the title compound as a white solid (0.025 g).

The title compound has a pKa 3.0 (measured using Method B), and pKa 6.3 (calculated using ACD).

MS (APCI+ve) 541/543 [M+H]$^+$ $^1$H NMR δ(DMSO-d$_6$) 1.54-1.64 (2H, m), 1.84-1.95 (2H, m), 2.12-2.35 (4H, m), 2.62-2.73 (2H, m), 2.92-3.00 (1H, m), 3.11-3.20 (1H, m), 3.53-3.61 (1H, m), 4.38-4.49 (1H, m), 4.56-4.76 (1H, br s), 6.98 (1H, dd), 7.25 (1H, d), 7.42-7.53 (6H, m), 8.11 (1H, t), 8.23 (1H, s).

EXAMPLE 13

5-Cyano-N-{(2R)-3-[4-(2,4-dichloro-3-methylphenoxy)piperidin-1-yl]-2-hydroxypropyl}-6-oxo-2-phenyl-1,6-dihydropyridine-3-carboxamide

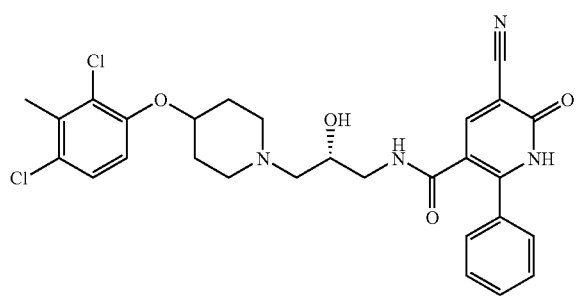

5-Cyano-6-oxo-2-phenyl-1,6-dihydropyridine-3-carboxylic acid (*European Journal of Medicinal Chemistry* 24 (5), 517-519, 1989; 0.112 g) was dissolved in thionyl chloride (4 mL) and heated under reflux for 2 h. The solvent was removed in vacuo and the residue was azeotroped with toluene (10 mL). The resultant pale yellow solid was dissolved in THF (4 mL) and added dropwise to a solution of (2R)-1-amino-3-[4-(2,4-dichloro-3-methylphenoxy)piperidin-1-yl]propan-2-ol (0.150 g) and triethylamine (0.7 mL) in DCM (2 mL). The mixture was stirred at room temperature overnight and the volatiles were removed in vacuo. The residue was dissolved in acetonitrile (6 mL) and purification by RPHPLC (Novapak, 0.1% ammonium acetate/acetonitrile) afforded the title compound as a dry yellow powder (0.011 g).

The title compound has a pKa 6.3 (calculated using ACD).

MS (APCI+ve) 555/557 [M+H]$^+$ $^1$H NMR δ(CDCl$_3$) 1.92-2.01 (2H, m), 2.06-2.21 (3H, m), 2.47 (3H, s), 2.50-2.56 (2H, m), 2.76-2.83 (1H, m), 2.87 (1H, td), 2.96-3.05 (2H, m), 3.06-3.15 (1H, m), 3.35-3.43 (1H, m), 4.50-4.55 (1H, m), 6.33-6.39 (1H, m), 6.74 (1H, d), 7.22 (1H, d), 7.47-7.51 (5H, m), 7.51-7.57 (1H, m), 8.22 (1H, s)

EXAMPLE 14

N-{(2R)-3-[4-(3,4-Dichlorophenoxy)piperidin-1-yl]-2-hydroxypropyl}-3-methyl-2,6-dioxo-1,2,3,6-tetrahydropyrimidine-4-carboxamide

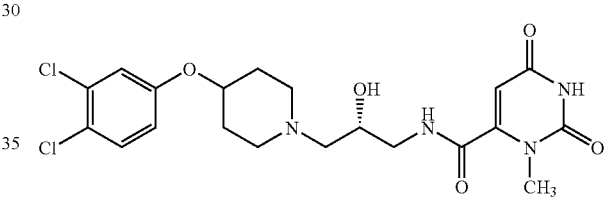

Step 1: 3-Methyl-2,6-dioxo-1,2,3,6-tetrahydropyrimidine-4-carboxylic acid

The subtitle compound was synthesized according to the procedure described in *Pharmazie* 48 1993, H. 11 861-862.

Step 2: N-{(2R)-3-[4-(3,4-Dichlorophenoxy)piperidin-1-yl]-2-hydroxypropyl}-3-methyl-2,6-dioxo-1,2,3,6-tetrahydropyrimidine-4-carboxamide 3-Methyl-2,6-dioxo-1,2,3,6-tetrahydropyrimidine-4-carboxylic acid (*Pharmazie* 48 1993, H. 11, 861-862; 0.173 g) was dissolved in thionyl chloride (8 mL) and heated under reflux for 2 h. The solvent was removed in vacuo and the residue was azeotroped with toluene (10 mL). The resultant pale yellow solid was dissolved in THF (4 mL) and added dropwise to a solution of (2R)-1-amino-3-[4-(3,4-dichlorophenoxy)piperidin-1-yl]propan-2-ol (0.325 g) and triethylamine (1.56 mL) in DCM (4.5 mL). The mixture was stirred at room temperature overnight and the volatiles were removed in vacuo. The residue was dissolved in acetonitrile (6 mL) and purification by RPHPLC (Novapak, 0.1% ammonium acetate/acetonitrile) followed by trituration with DCM afforded the title compound as a yellow powder (0.008 g).

The title compound has a pKa 6.9 (calculated using ACD).

MS (APCI+ve) 471/473 [M+H]$^+$

1H NMR δ (CD$_3$OD) 1.26-1.36 (2H, m), 1.78-1.85 (2H, m), 1.99-2.05 (2H, m), 2.55-2.60 (2H, m), 2.83-2.95 (2H, m), 3.11-3.14 (1H, m), 3.32 (3H, s), 3.49-3.52 (1H, m), 3.89-4.01 (1H, m), 4.41-4.47 (1H, m), 5.58 (1H, s), 5.78 (1H, d), 6.88-6.91 (1H, m), 7.11 (1H, d) 7.38 (1H, d).

EXAMPLE 15

N-{(2R)-3-[4-(3,4-Dichlorophenoxy)piperidin-1-yl]-2-hydroxypropyl}-2,6-dioxo-3-(2,2,2-trifluoroethyl)-1,2,3,6-tetrahydropyrimidine-4-carboxamide

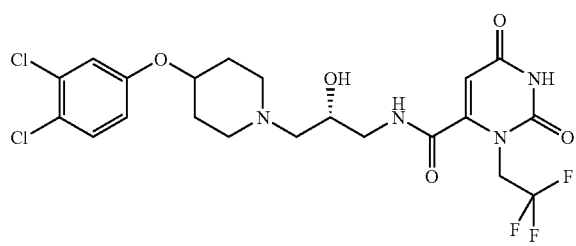

Step 1: 2,6-Dioxo-3-(2,2,2-trifluoroethyl)-1,2,3,6-tetrahydropyrimidine-4-carboxylic acid The subtitle compound was synthesised according to the procedure described in *Pharmazie* 48 1993, H. 11 861-862.

Step 2: N-{(2R)-3-[4-(3,4-Dichlorophenoxy)piperidin-1-yl]-2-hydroxypropyl}-2,6-dioxo-3-(2,2,2-trifluoroethyl)-1,2,3,6-tetrahydropyrimidine-4-carboxamide To a solution of (2R)-1-amino-3-[4-(3,4-dichlorophenoxy)piperidin-1-yl]propan-2-ol (0.134 g) in dry DMF (3 mL), was added N,N-diisopropylethylamine (0.14 mL), 2,6-dioxo-3-(2,2,2-trifluoroethyl)-1,2,3,6-tetrahydropyrimidine-4-carboxylic acid (0.100 g) and HATU (0.178 g). The reaction mixture was stirred at 0° C. under an atmosphere of nitrogen for 20 min, then quenched with saturated sodium bicarbonate solution (10 mL), and allowed to stand overnight. The mixture was extracted with ethyl acetate (3×10 mL). The combined organics were washed with brine (2×10 mL), dried over anhydrous magnesium sulfate, and the volatiles were removed in vacuo to give an oil (0.205 g). Purification by RPHPLC (Novapak, 0.1% ammonium acetate/acetonitrile) afforded the title compound (0.028 g) as a dry yellow powder.

The title compound has a pKa 5.9 (calculated using ACD).

MS (APCI+ve) 539/541(M+H)+

$^1$H NMR (CD$_3$OD) δ 1.83-1.68 (2H, m), 2.03-1.90 (2H, m), 2.29-2.24(1H, m), 2.45-2.34 (1H, m), 2.69-2.51 (4H, m), 2.97-2.84 (2H, m), 3.03 (1H, quintet, 3.26-3.23 (1H, m), 3.34-3.32 (1H, m), 3.37-3.35 (1H, m), 3.90 (1H, quintet), 4.40 (1H, quintet), 5.39 (1H, s), 5.93 (1H, s), 6.82 (1H, dd), 7.04 (1H, d) 7.30 (1H, d).

EXAMPLE 16

5-Cyano-2-cyclopropyl-N-[(2R)-3-[4-(3,4-dichlorophenoxy)-1-piperidinyl]-2-hydroxypropyl]-1,6-dihydro-6-oxo-3-pyridinecarboxamide

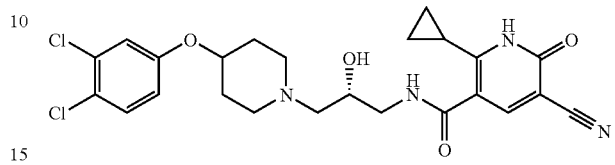

A stirred solution of 5-cyano-2-cyclopropyl-6-oxo-1,6-dihydropyridine-3-carboxylic acid (0.080 g) (*J. Med. Chem.* 2002, 45, 1887) in thionyl chloride (2.5 mL) was heated at reflux for 2 h. Thionyl chloride was removed from the cooled solution in vacuo. The residue was dissolved in THF (4 mL) and this solution was added dropwise at room temperature to a solution of (2R)-1-amino-3-[4-(3,4-dichlorophenoxy)piperidin-1-yl]propan-2-ol (0.125 g) and triethylamine (0.7 mL) in DCM (2 mL) before stirring overnight. The reaction mixture was concentrated in vacuo and redissolved in 9:1 acetonitrile/water (4 mL) before subjecting to RPHPLC (gradient 0.1% ammonium acetate/acetonitrile 95% to 50%) to yield a white solid (0.022 g).

The title compound has a pKa 3.8 (measured using Method B), and pKa 7.5 (calculated using ACD).

MS (ES+ve) 505/507 [M+H]+

$^1$H NMR δ (DMSO-d$_6$) 1.02-1.08 (2H, m), 1.11-1.17 (2H, m), 1.57-1.68 (2H m), 1.89-1.97 (2H, m), 2.30-2.43 (4H, m), 2.53-2.61 (1H, m), 2.72-2.85 (2H, m), 3.05-3.14 (1H, m), 3.74-3.81 (1H, m), 4.42-4.49 (1H, m), 6.98 (1H, dd), 7.26 (1H, d), 7.50 (1H, d), 8.10 (1H, s), 8.32 (1H, t); resonance at ~3.3 (1H, m) obscured by HDO.

EXAMPLE 17

5-Cyano-2-cyclopropyl-N-[(2R)-3-[4-(2,4-dichloro-3-methylphenoxy)-1-piperidinyl]-2-hydroxypropyl]-1,6-dihydro-6-oxo-3-pyridinecarboxamide

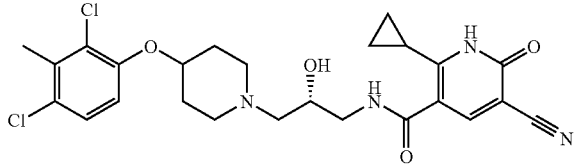

The title compound has pKa 7.5 (calculated using ACD).

MS (ES+ve) 519/521 [M+H]+

$^1$H NMR δ (DMSO-d$_6$) 1.00-1.07 (2H, m), 1.10-1.17 (2H, m), 1.62-1.73 (2H, m), 1.86-1.93 (2H, m), 2.30-2.39 (4H, m), 2.40 (3H, s), 2.52-2.61 (1H, m), 2.66-2.78 (2H, m), 3.04-3.13

(1H, m), 3.73-3.80 (1H, m), 4.46-4.54 (1H, m), 7.10 (1H, d), 7.35 (1H, d), 8.07 (1H, s), 8.29 (1H, t); resonance at ~3.3 (1H, m) obscured by HDO.

EXAMPLE 18

N-{(2R)-3-[4-(3,4-Dichlorophenoxy)piperidin-1-yl]-2-hydroxypropyl}-6-[(methylsulfonyl)amino]-4-(trifluoromethyl)nicotinamide

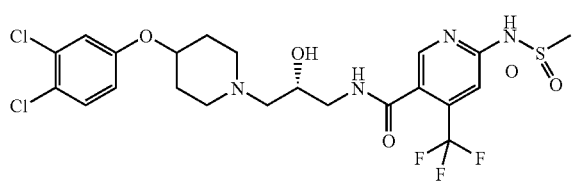

Step 1: 6-Chloro-N-{(2R)-3-[4-(3,4-dichlorophenoxy)piperidin-1-yl]-2-hydroxypropyl}-4-(trifluoromethyl)nicotinamide A solution of 4-trifluoromethyl-6-chloronicotinoyl chloride (0.585 g) in THF (3 mL) was added dropwise at room temperature to a stirred solution of (2R)-1-amino-3-[4-(3,4-dichlorophenoxy)piperidin-1-yl]propan-2-ol (0.735 g) and triethylamine (0.7 mL) in DCM (2 mL). After 18 h, the reaction mixture was concentrated in vacuo and subjected to flash column chromatography (eluent 96:4 dichloromethane/7 N ammonia in methanol) to yield a yellow oil (1.02 g). A small amount (0.1 g) was redissolved in 9:1 acetonitrile/water (4 mL) and subjected to RPHPLC (gradient 0.1% ammonium acetate/acetonitrile 95% to 5%) to yield a white solid (0.025 g).

MS (ES+ve) 526/528 [M+H]$^+$ $^1$H NMR δ (CD$_3$OD) 1.66-1.80 (2H, m), 1.87-2.00 (2H, m), 2.42-2.57 (4H, m), 2.76-2.90 (2H, m), 3.27 (1H, dd), 3.44 (1H, dd), 3.86-3.95 (1H, m), 4.30-4.41 (1H, m), 6.80 (1H, dd), 7.02 (1H, d), 7.29 (1H, d), 7.78 (1H, s), 8.56 (1H, s).

Step 2: N-{(2R)-3-[4-(3,4-Dichlorophenoxy)piperidin-1-yl]-2-hydroxypropyl}-6-[(methylsulfonyl)amino]-4-(trifluoromethyl)nicotinamide A stirred solution of 6-chloro-N-{(2R)-3-[4-(3,4-dichlorophenoxy)piperidin-1-yl]-2-hydroxypropyl}-4-(trifluoromethyl)nicotinamide (0.28 g), methanesulfonamide (0.12 g) and potassium carbonate (0.148 g) in N-methyl-2-pyrrolidinone was heated under microwave irradiation (100 W) at 100° C. for 15 min. The reaction mixture was concentrated in vacuo and redissolved in 4:1:1 acetonitrile/water/acetic acid (6 mL) and subjected to RPHPLC (gradient 0.1% ammonium acetate/acetonitrile 95% to 5%) to yield a white solid (0.025 g).

The title compound has a pKa 5.3 (measured using Method B).

MS (ES+ve) 585/587 [M+H]$^+$ $^1$H NMR δ(CD$_3$OD) 1.86-2.02 (2H, m), 2.06-2.20 (2H, m), 2.74-2.98 (4H, m), 3.07-3.22 (2H, m), 3.24 (3H, s), 3.36-3.56 (2H, m), 4.05-4.16 (1H, m), 4.52-4.62 (1H, m), 6.95 (1H, dd), 7.12 (1H, s), 7.18 (1H, d), 7.42 (1H, d), 8.44 (1H, s)

EXAMPLE 19

N-{(2R)-3-[4-(3,4-Dichlorophenoxy)piperidin-1-yl]-2-hydroxypropyl}-5-[(2,2,2-trifluoroethyl)thio]-1H-1,2,3-triazole-4-carboxamide

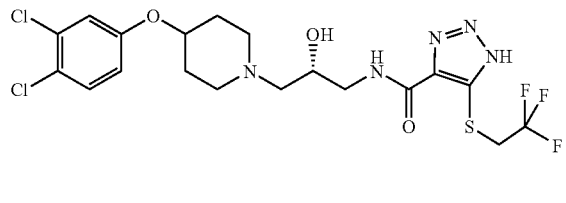

Step 1: Ethyl 1-(4-methoxybenzyl)-5-[(2,2,2-trifluoroethyl)thio]-1H-1,2,3-triazole-4-carboxylate Sodium hydride (0.018 g) was added to a solution of 3,3,3-trifluoroethanol (0.060 mL) in dry DMF (1.5 mL). After stirring at room temperature for 30 min a solution of ethyl 5-chloro-1H-1,2,3-triazole-4-carboxylate (0.20 g, J. Chem. Soc. Perkin I, 1982, 627) in dry DMF (1 mL) was added. The mixture was heated at 80° C. for 18 h then cooled and partitioned between diethyl ether (50 mL) and water (50 mL). The aqueous layer was re-extracted with diethyl ether (2×50 mL) and the combined extracts were dried over anhydrous sodium sulfate. Concentration in vacuo and chromatography on silica (0-50% gradient EtOAc/isohexane) gave the subtitle compound (0.127 g).

MS (ES+ve) 376 [M+H]$^+$ $^1$H NMR δ(CDCl$_3$) 1.44 (3H, t), 3.66 (2H, q), 3.78 (3H, s), 4.46 (2H, q), 5.62 (2H, s), 6.89-6.83 (2H, m), 7.29-7.24 (2H, m).

Step 2: Ethyl 5-[(2,2,2-trifluoroethyl)thio]-1H-1,2,3-triazole-4-carboxylate Ethyl 1-(4-methoxybenzyl)-5-[(2,2,2-trifluoroethyl)thio]-1H-1,2,3-triazole-4-carboxylate (0.127 g) was dissolved in trifluoroacetic acid (2 mL) and heated at 65° C. for 4 h. The trifluoroacetic acid was evaporated in vacuo and the residue was azeotroped with toluene (3×10 mL) then dried under vacuum to afford the subtitle compound (0.086 g).

MS (ES−ve) 234 [M−HF]$^-$ $^1$H NMR δ(CDCl$_3$) 1.44 (3H, t), 3.89 (2H, q), 4.46 (2H, q).

Step 3: 5-[(2,2,2-Trifluoroethyl)thio]-1H-1,2,3-triazole-4-carboxylic acid

Ethyl 5-[(2,2,2-trifluoroethyl)thio]-1H-1,2,3-triazole-4-carboxylate (0.086 g) was suspended in 1N aqueous sodium hydroxide solution and heated at 70° C. for 3 h. The reaction mixture was filtered and then acidified with concentrated hydrochloric acid. Concentration in vacuo afforded a colourless solid which was washed with ice cold water to afford the subtitle compound (0.080 g)

MS (ES−ve) 226 [M−H]−

$^1$H NMR δ(DMSO-d$_6$) 4.09-4.22 (2H, m), 13.51 (1H, s), 15.75 (1H, s).

Step 4: N-{(2R)-3-[4-(3,4-Dichlorophenoxy)piperidin-1-yl]-2-hydroxypropyl}-5-[(2,2,2-trifluoroethyl)thio]-1H-1,2,3-triazole-4-carboxamide 5-[(2,2,2-Trifluoroethyl)thio]-1H-1,2,3-triazole-4-carboxylic acid (0.080 g) was dissolved in DCM (2 mL) and treated with oxalyl chloride (0.060 mL) and DMF (1 drop). The solution was stirred at room temperature for 1 h then concentrated in vacuo and azeotroped with anhydrous toluene (5 mL). The residue was redissolved in dry THF and added dropwise to a stirred solution of (2R)-1-amino-3-[4-(3,4-dichlorophenoxy)piperidin-1-yl]propan-2-ol (0.108 g) and triethylamine (0.142 mL) in DCM. The mixture was stirred for 1 h, the solvent was evaporated in vacuo and the product purified by RPHPLC (gradient 0.1% ammonium acetate/acetonitrile 50% to 5%) to afford the title compound as a colourless solid (0.058 g).

The title compound has a pKa 5.2 (measured using Method B), and pKa 4.6 (calculated using ACD).

MS (ES+ve) 528/530 [M+H]+

$^1$H NMR δ(CD$_3$OD) 1.92-1.84 (2H, m), 2.09-1.98 (2H, m), 2.92-2.72 (4H, m), 3.13-3.04 (2H, m), 3.42-3.32 (2H, m), 3.82 (2H, q), 4.03-3.97 (1H, m), 4.50-4.43 (1H, m), 6.83 (1H, dd), 7.07 (1H, d), 7.30 (1H, d).

EXAMPLE 20

4-[({(2R)-3-[4-(3,4-Dichlorophenoxy)piperidin-1-yl]-2-hydroxypropyl}amino)-carbonyl]-1-naphthoic acid

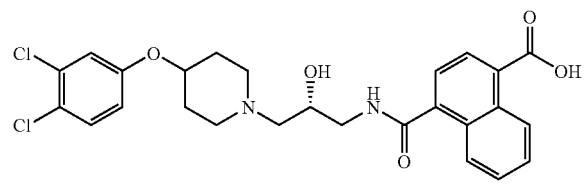

To a solution of naphthalene-1,4-dicarboxylic acid (0.100 g), (2R)-1-amino-3-[4-(3,4-dichlorophenoxy)piperidin-1-yl]propan-2-ol (0.147 g) and triethylamine (0.193 mL) in N-methyl-2-pyrolidinone (20 mL) was added PyBrOP (0.258 g). The reaction mixture was stirred for 16 h and the solvent was removed in vacuo. The residue was purified by RPHPLC (Symmetry, 0.1% ammonium acetate/acetonitrile) to afford the title compound as a colourless solid (0.050 g, 20%).

The title compound has pKa 3.1 (calculated using ACD).

MS (APCI+ve) 517/519 [M+H]+

$^1$H NMR δ(CD$_3$OD) 2.02-2.30 (4H, m), 3.09-3.20 (2H, m), 3.22-3.30 (2H, m), 3.38-3.47 (2H, m), 3.51-3.67 (2H, m), 4.26-4.35 (1H, m), 4.66-4.73 (1H, m), 6.99 (1H, dd), 7.23 (1H, d), 7.45 (1H, d), 7.53-7.59 (2H, m), 7.64 (1H, d), 7.69 (1H, d), 8.23-8.26 (1H, m), 8.57-8.60 (1H, m).

EXAMPLE 21

N-{(2R)-3-[4-(3,4-Dichlorophenoxy)piperidin-1-yl]-2-hydroxypropyl}-2-[(methylsulfonyl)amino]-4-(trifluoromethyl)-1,3-thiazole-5-carboxamide

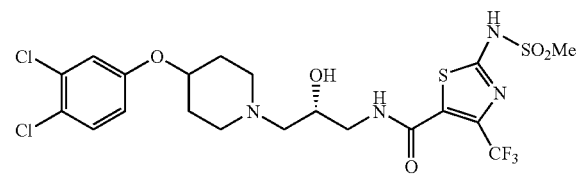

Step 1: 2-[(Methylsulfonyl)amino]-4-(trifluoromethyl)-1,3-thiazole-5-carboxylic acid To a stirred solution of ethyl-2-amino-4-(trifluoromethyl)-5-thiazole carboxylate (1.2 g) and triethylamine (2.1 mL) in THF (12 mL) was added methane sulfonic anhydride (1.74 g) in small portions at room temperature. After 2 h, the reaction mixture was concentrated in vacuo and the residue was stirred in dioxane (5 mL) and aqueous 1 N NaOH (5 mL) for 16 h. The reaction mixture was concentrated in vacuo and to the residue in water (20 mL) and THF (30 mL) was added lithium hydroxide monohydrate (1.8 g) before being heated at 50° C. for 12 h. To the cooled reaction mixture was added 1 N aqueous hydrochloric acid (30 mL) and extracted into EtOAc (2×25 mL), dried over sodium sulfate, filtered, and concentrated in vacuo.

$^1$H NMR δ(DMSO-d$_6$) 3.26 (3H, m).

Step 2: N-{(2R)-3-[4-(3,4-Dichlorophenoxy)piperidin-1-yl]-2-hydroxypropyl}-2-[(methylsulfonyl)amino]-4-(trifluoromethyl)-1,3-thiazole-5-carboxamide A stirred solution of 2-[(methylsulfonyl)amino]-4-(trifluoromethyl)-1,3-thiazole-5-carboxylic acid (0.145 g) in thionyl chloride (3 mL) was heated at reflux for 2 h. Thionyl chloride was removed from the cooled solution in vacuo. The residue was dissolved in THF (4 mL) and this solution was added dropwise at room temperature to a solution of (2R)-1-amino-3-[4-(3,4-dichlorophenoxy)piperidin-1-yl]propan-2-ol (0.144 g) and triethylamine (0.7 mL) in DCM (2 mL) before stirring overnight. The reaction mixture was concentrated in vacuo and redissolved in 9:1 acetonitrile/water (4 mL) before being subjected to RPHPLC (Novapak, gradient 0.1% ammonium acetate/acetonitrile 95% to 50%) to yield a white solid (0.028 g).

Retention time: 1.46 min (reverse phase analytical HPLC (Hewlett Packard Series 1100): Waters "Symmetry" C8 column 3.5 μm; 4.6×50 mm column gradient 0.1% ammonium acetate/acetonitrile 75% to 5% in 3 min; flow 2 mL/min).

The title compound has a pKa 7.5 (measured using Method B).

MS (ES+ve) 591/593 [M+H]+

$^1$H NMR δ(CD$_3$OD) 1.88-2.04 (2H, m), 2.05-2.19 (2H, m), 2.82 (3H, s), 2.97 (1H, t), 3.10 (1H, d), 3.14-3.41 (4H, m), 4.05-4.14 (1H, m), 4.55-4.62 (1H, m), 6.87 (1H, dd), 7.12 (1H, d), 7.32 (1H, d), 2 resonances obscured.

EXAMPLE 22

N-{(2R)-3-[4-(4-Chloro-2-methylphenoxy)piperidin-1-yl]-2-hydroxypropyl}-2-oxo-4-(trifluoromethyl)-2,3-dihydro-1,3-thiazole-5-carboxamide

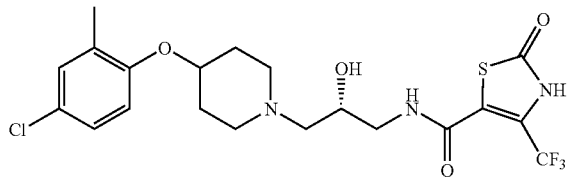

Prepared as Example 4 from (2R)-1-amino-3-[4-(4-chloro-2-methylphenoxy)-piperidin-1-yl]propan-2-ol [WO2003068743(A1)] to give a white solid (0.046 g).

Retention time: 1.37 min (reverse phase analytical HPLC (Hewlett Packard Series 1100): Waters "Symmetry" C8 column 3.5 µm; 4.6×50 mm column gradient 0.1% ammonium acetate/acetonitrile 75% to 5% in 3 min; flow 2 mL/min).

The title compound has pKa 6.1 (calculated using ACD).
MS (ES+ve) 494/496 [M+H]$^+$
$^1$H NMR δ(CD$_3$OD) 1.97-2.10 (2H, m), 2.11-2.21 (2H, m), 2.22 (3H, s), 2.93 (1H, dd), 3.02 (1H, dd), 3.08-3.21 (2H, m), 3.21-3.30 (2H, m), 3.33-3.42 (2H, m), 4.06-4.13 (1H, m), 4.57-4.63 (1H, m), 6.92 (1H, d), 7.11 (1H, dd), 7.15 (1H, d).

EXAMPLE 23

[5-[({(2R)-3-[4-(3,4-Dichlorophenoxy)piperidin-1-yl]-2-hydroxypropyl}amino)carbonyl]-2-oxo-4-(trifluoromethyl)pyridin-1(2H)-yl]acetic acid

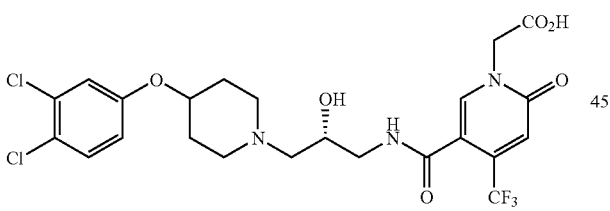

Step 1: 1-(2-Methoxy-2-oxoethyl)-6-oxo-4-(trifluoromethyl)-1,6-dihydropyridine-3-carboxylic acid To a stirred suspension of 6-oxo-4-(trifluoromethyl)-1,6-dihydropyridine-3-carboxylic acid (0.207 g) and potassium carbonate (0.553 g) in methanol (5 mL) was added methyl bromoacetate (0.104 mL) at room temperature. After 16 h, the reaction was not complete, so further methyl bromoacetate (0.15 mL) was added. After a further 16 h, the mixture was concentrated in vacuo before the addition of 1 N aqueous hydrochloric acid (30 mL) and extracted into ethyl acetate (3×25 mL), dried over Na$_2$SO$_4$, filtered, and concentrated in vacuo to leave a white solid (300 mg).

MS (ES−ve) 278 [M−H]$^-$
$^1$H NMR δ(DMSO-d$_6$) 3.70 (3H, s), 4.88 (2H, s), 6.91 (1H, d), 8.68 (1H, d), 13.25 (1H, br s).

Step 2: Methyl[5-[({(2R)-3-[4-(3,4-dichlorophenoxy)piperidin-1-yl]-2-hydroxypropyl}amino)carbonyl]-2-oxo-4-(trifluoromethyl)pyridin-1(2H)-yl]acetate A stirred solution of 1-(2-methoxy-2-oxoethyl)-6-oxo-4-(trifluoromethyl)-1,6-dihydropyridine-3-carboxylic acid (0.140 g) in thionyl chloride (4 mL) was heated at reflux for 2 h. Thionyl chloride was removed from the cooled solution in vacuo. The residue was dissolved in THF (4 mL) and this solution was added dropwise at room temperature to a solution of (2R)-1-amino-3-[4-(3,4-dichlorophenoxy)piperidin-1-yl]propan-2-ol (0.144 g) and triethylamine (0.7 mL) in DCM (2 mL) before stirring overnight. The reaction mixture was concentrated in vacuo and used directly in the subsequent step.

Step 3: [5-[({(2R)-3-[4-(3,4-Dichlorophenoxy)piperidin-1-yl]-2-hydroxypropyl}amino)carbonyl]-2-oxo-4-(trifluoromethyl)pyridin-1(2H)-yl]acetic acid A solution of methyl[5-[({(2R)-3-[4-(3,4-dichlorophenoxy)piperidin-1-yl]-2-hydroxypropyl}amino)carbonyl]-2-oxo-4-(trifluoromethyl)pyridin-1(2H)-yl]acetate (0.1 g) and lithium hydroxide (0.022 g) in THF (3 mL) and water (1 mL) was stirred at room temperature for 16 h. The reaction mixture was concentrated in vacuo and redissolved in 9:1 acetonitrile/water (4 mL), and acidified to pH 5 with acetic acid before being subjected to reverse phase HPLC (Novapak, gradient 0.1% ammonium acetate/acetonitrile 95% to 50%) to yield a white solid (0.032 g).

Retention time: 1.29 min (reverse phase analytical HPLC (Hewlett Packard Series 1100): Waters "Symmetry" C8 column 3.5 µm; 4.6×50 mm column gradient 0.1% ammonium acetate/acetonitrile 75% to 5% in 3 min; flow 2 mL/min).

The title compound has pKa 3.6 (calculated using ACD).
MS (ES+ve) 566/568 [M+H]$^+$
$^1$H NMR δ(CD$_3$OD) 1.97-2.07 (2H, m), 2.08-2.23 (2H, m), 2.93 (1H, dd), 3.03 (1H, dd), 3.06-3.16 (2H, m), 3.21-3.29 (2H, m), 3.36 (1H, dd), 3.45 (1H, dd), 4.08-4.15 (1H, m), 4.58 (2H, d), 4.59-4.65 (1H, m), 6.85 (1H, s), 6.95 (1H, dd), 7.19 (1H, d), 7.41 (1H, d), 8.07 (1H, s).

EXAMPLE 24

N-{(2R)-3-[4-(3,4-Dichloro-2-methylphenoxy)piperidin-1-yl]-2-hydroxypropyl}-2-oxo-4-(trifluoromethyl)-2,3-dihydro-1,3-thiazole-5-carboxamide

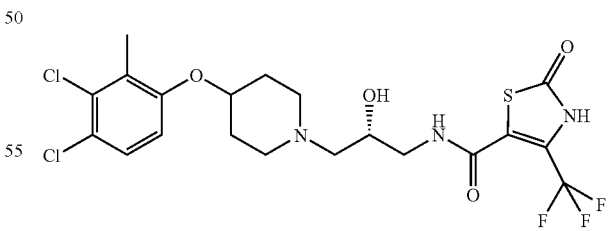

The title compound was prepared as Example 4 and was obtained as a white solid (0.10 g).

The title compound has pKa 6.1 (calculated using ACD).
MS (APCI+ve) 528/530 [M+H]$^+$
$^1$H NMR δ(CD3OD) 1.87-2.02 (2H, m), 2.02-2.21 (2H, m), 2.25 (3H, s), 2.79-2.97 (2H, m), 2.97-3.20 (2H, m), 3.22-3.33 (4H, m), 4.00 (1H, td), 4.54 (1H, s), 6.87 (1H, d), 7.21 (1H, dd).

EXAMPLE 25

N-{(2R)-3-[4-(3,4-Dichlorophenoxy)piperidin-1-yl]-2-hydroxypropyl}-4-(4-fluorophenyl)-2-oxo-2,3-dihydro-1,3-thiazole-5-carboxamide

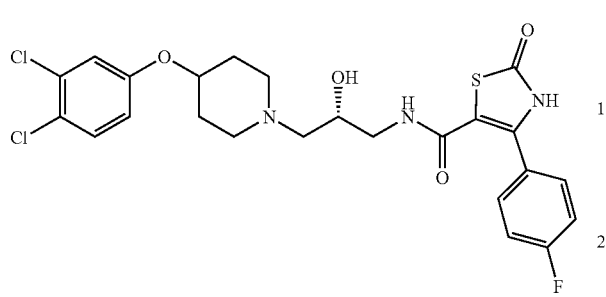

Step 1: Methyl 4-(4-fluorophenyl)-2-oxo-2,3-dihydro-1,3-thiazole-5-carboxylate Prepared according to *J. Het. Chem.* 22, 1985, 1621-30 using methyl (2E)-3-amino-3-(4-fluorophenyl)acrylate [*Angew. Chem.* 2003, 42(8), 913-6]. Obtained as a yellow solid (3.67 g).

Retention time: 2.62 min (reverse phase analytical HPLC (Hewlett Packard Series 1100): Waters "Symmetry" C8 column 3.5 μm; 4.6×50 mm column gradient 0.1% ammonium acetate/acetonitrile 95% to 50% in 3 min; flow 2 mL/min).

MS (ES−ve) 252 [M−H]−

Step 2: 4-(4-Fluorophenyl)-2-oxo-2,3-dihydro-1,3-thiazole-5-carboxylic acid

Prepared as for Example 4. Obtained as pale yellow solid (0.38 g).

MS (ES+ve) 240 [M+H]+

$^1$H NMR δ(DMSO-d6) 7.24-7.33 (2H, m), 7.57-7.64 (2H, m), 12.10 (1H, s).

Step 3: N-{(2R)-3-[4-(3,4-Dichlorophenoxy)piperidin-1-yl]-2-hydroxypropyl}-4-(4-fluorophenyl)-2-oxo-2,3-dihydro-1,3-thiazole-5-carboxamide Prepared as Example 4. Obtained as white solid (0.06 g).

The title compound has a pKa 7.4 (measured using Method B).

MS (APCI+ve) 538/540 [M+H]+

$^1$H NMR δ(DMSO-$d_6$) 1.51-1.63 (2H, m), 1.83-1.93 (2H, m), 2.15-2.29 (4H, m), 2.59-2.71 (2H, m), 2.97-3.04 (1H, m), 3.15-3.21 (1H, m), 3.60 (1H, quintet), 4.42 (1H, septet), 4.60 (1H, s), 6.98 (1H, dd), 7.25 (1H, d), 7.26-7.34 (3H, m), 7.49 (1H, d), 7.56 (2H, q).

EXAMPLE 26

N-{(2R)-3-[4-(3,4-Dichlorophenoxy)piperidin-1-yl]-2-hydroxypropyl}-5-(4-fluorophenyl)-1H-1,2,3-triazole-4-carboxamide

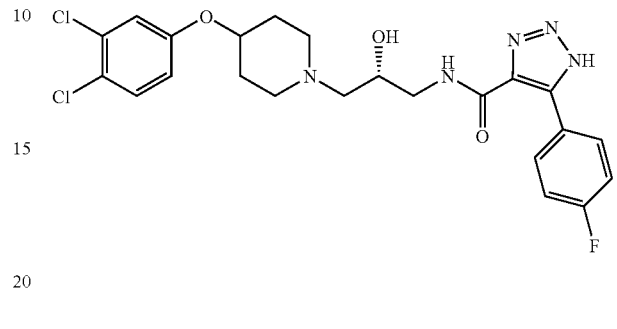

Step 1: Methyl 5-(4-fluorophenyl)-1H-1,2,3-triazole-4-carboxylate

Sodium (0.25 g) was added gradually to dry absolute ethanol (4.6 mL). Methyl 3-(4-fluorophenyl)-3-oxopropanoate (1.44 g) was added followed by 4-methoxybenzyl azide. The mixture was heated at reflux for 18 h and was then cooled and concentrated in vacuo. The mixture was poured into ice water and acidified with dilute hydrochloric acid. The resulting precipitate was filtered and dried to yield a yellow solid. This was heated at 65° C. in trifluoroacetic acid (8 mL) for 8 h. The mixture was concentrated in vacuo and azeotroped with toluene and then treated with ethyl acetate and filtered to yield the title compound as a yellow solid (0.5 g). Used without purification.

Step 2: 5-(4-Fluorophenyl)-1H-1,2,3-triazole-4-carboxylic acid

Prepared as for Example 8. Obtained as a white solid.

Retention time: 0.87 min (reverse phase analytical HPLC (Hewlett Packard Series 1100): Waters "Symmetry" C8 column 3.5 μm; 4.6×50 mm column gradient 0.1% ammonium acetate/acetonitrile 95% to 50% in 3 min; flow 2 mL/min).

MS (ES−ve) 206 [M−H]−

Step 3: N-{(2R)-3-[4-(3,4-Dichlorophenoxy)piperidin-1-yl]-2-hydroxypropyl}-5-(4-fluorophenyl)-1H-1,2,3-triazole-4-carboxamide Prepared as Example 8. Obtained as white solid (0.10 g).

The title compound has a pKa 6.1 (measured using Method B).

MS (APCI+ve) 508/510 [M+H]+

$^1$H NMR δ(DMSO-$d_6$) 1.59-1.70 (2H, m), 1.87-1.97 (2H, m), 2.28-2.46 (4H, m), 2.67-2.82 (2H, m), 3.24-3.41 (2H, m), 3.81 (1H, quintet), 4.45 (1H, septet), 4.86 (1H, s), 6.98 (1H, dd), 7.26 (1H, t), 7.29 (2H, tt), 7.49 (1H, d), 7.99-8.04 (2H, m), 8.44 (1H, t).

EXAMPLE 27

N-{(2R)-3-[4-(3-Chloro-4-cyanophenoxy)piperidin-1-yl]-2-hydroxypropyl}-2-oxo-4-(trifluoromethyl)-2,3-dihydro-1,3-thiazole-5-carboxamide

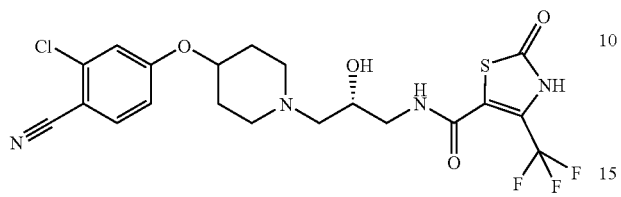

The title compound was obtained as a white solid (0.07 g). The title compound has pKa 6.1 (calculated using ACD).
MS (APCI+ve) 505/507 [M+H]$^+$
$^1$H NMR δ(DMSO-d$_6$) 1.69-1.82 (2H, m), 1.95-2.06 (2H, m), 2.51-2.67 (4H, m), 2.87-2.95 (2H, m), 3.15-3.29 (2H, m), 3.80 (1H, quintet), 4.65 (1H, septet), 7.10 (1H, dd), 7.30 (1H, d), 7.52 (1H, s), 7.79 (1H, d).

EXAMPLE 28

N-{(2S)-3-[4-(3,4-Dichlorophenoxy)piperidin-1-yl]-2-hydroxypropyl}-2-oxo-4-(trifluoromethyl)-2,3-dihydro-1,3-thiazole-5-carboxamide

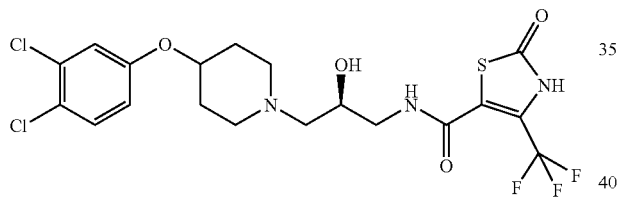

The title compound was obtained as a white solid (0.14 g). The title compound has pKa 6.1 (calculated using ACD).
MS (APCI+ve) 514/516(M+H)$^+$
$^1$H NMR δ(DMSO-d$_6$ 90° C.) 1.69-1.82 (2H, m), 1.92-2.06 (2H, m), 2.52-2.75 (4H, m), 2.88-3.13 (2H, m), 3.83 (1H, quintet), 4.50 (1H, septet), 6.98 (1H, dd), 7.23 (1H, d), 7.47 (1H, d), 7.53 (1H, s).

EXAMPLE 29

N-{(2S)-3-[4-(3-Chloro-4-cyanophenoxy)piperidin-1-yl]-2-hydroxypropyl}-N-methyl-2-oxo-4-(trifluoromethyl)-2,3-dihydro-1,3-thiazole-5-carboxamide

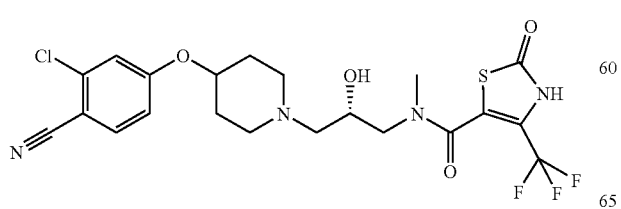

The title compound was obtained as a white solid (0.13 g). The title compound has pKa 6.3 (calculated using ACD).
MS (APCI+ve) 519/521 [M+H]$^+$
$^1$H NMR δ(DMSO-d$_6$ 90° C.) 1.65-1.79 (2H, m), 1.91-2.03 (2H, m), 2.35-2.59 (4H obscured, m), 2.80-2.89 (2H obscured, m), 3.00 (3H obscured, s), 3.23 (1H, dd), 3.53 (1H, dd), 3.90 (1H, quintet), 4.62 (1H, septet), 7.09 (1H, dd), 7.30 (1H, d), 7.79 (1H, d).

EXAMPLE 30

N-{(2R)-3-[4-(2,4-Dichloro-3-methylphenoxy)piperidin-1-yl]-2-hydroxypropyl}-2-oxo-4-(trifluoromethyl)-2,3-dihydro-1,3-thiazole-5-carboxamide

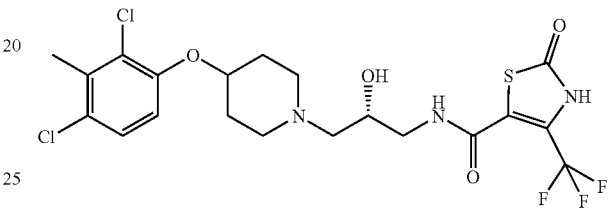

The title compound was obtained as a white solid (0.08 g). The title compound has pKa 6.1 (calculated using ACD).
MS (APCI+ve) 528/530 [M+H]$^+$
$^1$H NMR δ(DMSO-d$_6$) 1.74-1.87 (2H, m), 1.93-2.05 (2H, m), 2.41 (3H, s), 2.51-2.72 (4H, m), 2.88-2.98 (2H, m), 3.14-3.30 (2H, m), 3.82 (1H, quintet), 4.52 (1H, septet), 7.07 (1H, d), 7.32 (1H, d), 7.54 (1H, s).

EXAMPLE 31

N-{(2R)-3-[4-(3-Chloro-4-cyanophenoxy)piperidin-1-yl]-2-hydroxypropyl}-5-isopropyl-1H-1,2,3-triazole-4-carboxamide

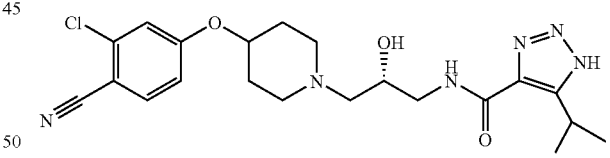

Step 1: Ethyl 5-isopropyl-1H-1,2,3-triazole-4-carboxylate

Prepared as Example 8 using ethyl 4-methyl-3-oxopentanoate. Used without purification.

Step 2: 5-iso-Propyl-1H-1,2,3-triazole-4-carboxylic acid

Prepared as Example 8 to yield an amber oily solid.
MS (ES+ve)156 [M+H]$^+$
Retention time: 0.49 min (reverse phase analytical HPLC (Hewlett Packard Series 1100): Waters "Symmetry" C8 column 3.5 μm; 4.6×50 mm column gradient 0.1% ammonium acetate/acetonitrile 95% to 50% in 3 min; flow 2 mL/min).

Step 3: N-{(2R)-3-[4-(3-chloro-4-cyanophenoxy) piperidin-1-yl]-2-hydroxypropyl}-5-isopropyl-1H-1, 2,3-triazole-4-carboxamide The title compound was prepared as Example 8 and obtained as a white solid (0.04 g).
The title compound has pKa 7.3 (calculated using ACD).
MS (APCI+ve) 447/449 [M+H]$^+$
1H NMR δ(DMSO-d$_6$ 90° C.) 1.25 (6H, d), 1.64-1.74 (2H, m), 1.89-1.99 (2H, m), 2.30-2.43 (4H, m), 2.68-2.79 (2H, m), 3.29 (1H, dt), 3.39 (1H, dt), 3.65 (1H, septet), 3.78 (1H, quintet), 4.57 (1H, septet), 4.58 (1H, s), 7.08 (1H, dd), 7.28 (1H, d), 7.78 (1H, d), 7.96 (1H, s).

EXAMPLE 32

N-{(2S)-3-[4-(3-Chloro-4-cyanophenoxy)piperidin-1-yl]-2-hydroxypropyl}-5-isopropyl-N-methyl-1H-1, 2,3-triazole-4-carboxamide

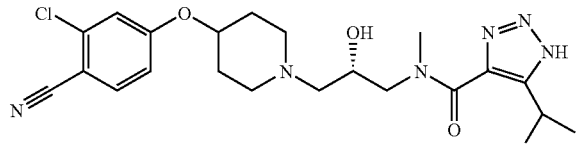

The title compound was prepared as Example 8 and obtained as a white solid (0.03 g).
The title compound has pKa 8.0 (calculated using ACD).
MS (APCI+ve) 461/463 [M+H]$^+$
$^1$H NMR δ(DMSO-d$_6$) 1.22 (6H, d), 1.54-1.70 (2H, m), 1.83-1.95 (2H, m), 2.19-2.39 (4H, m), 2.56-2.76 (2H, m), 3.09 (3H, s), 3.18-3.35 (2H, m), 3.68 (1H, dd), 3.87 (1H, s), 4.54 (1H, s), 7.07 (1H, dd), 7.26 (1H, s), 7.78 (1H, d).

EXAMPLE 33

N-{(2R)-3-[4-(3,4-Dichlorophenoxy)piperidin-1-yl]-2-hydroxypropyl}-2-oxo-4-(2,2,2-trifluoroethyl)-2,3-dihydro-1,3-thiazole-5-carboxamide

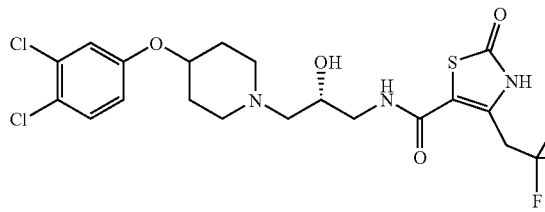

Step 1: Benzyl 5,5,5-trifluoro-3-oxopentanoate 3,3,3-Trifluoropropanoic acid (5 g) in dry THF (50 mL) was treated with N,N-carbonyldiimidazole (7.6 g) and the mixture was stirred at room temperature for 6 h. 2,2-Dimethyl-1,3-dioxane-4,6-dione (5.63 g) and triethylamine (5.4 mL) were added and the mixture was stirred at room temperature for 18 h. Aqueous potassium hydrogen sulphate solution (10% w/v) was added and the mixture was extracted with diethyl ether. The organic layer was separated and washed with water, then brine and dried over sodium sulphate and filtered. The solvent was concentrated in vacuo to yield a pale yellow solid. Toluene was added, followed by benzyl alcohol. The mixture was heated at 80° C. for 6 h and was then concentrated in vacuo. Purification by flash chromatography (eluent 5:95 ethyl acetate/isohexane) yielded the title compound as a beige solid (3.1 g).
MS (ES−ve) 259 [M−H]$^−$
$^1$H NMR δ(CDCl$_3$) 3.41 (2H, q), 3.58 (2H, s), 5.19 (2H, s), 7.30-7.42 (5H, m).

Step 2: Benzyl (2E)-3-amino-5,5,5-trifluoropent-2-enoate

Benzyl 5,5,5-trifluoro-3-oxopentanoate (2.1 g) in ethanol (15 mL) was treated with ammonium acetate (2 g). The mixture was heated at 80° C. for 18 h and was then concentrated in vacuo. Water and DCM were added. The organic phase was separated and washed with sodium bicarbonate solution and water and then dried over sodium sulphate and filtered. The solvent was concentrated in vacuo to yield the title compound as a colourless oil (0.71 g).
Retention time: 3.34 min (reverse phase analytical HPLC (Hewlett Packard Series 1100): Waters "Symmetry" C8 column 3.5 μm; 4.6×50 mm column gradient 0.1% ammonium acetate/acetonitrile 95% to 50% in 3 min; flow 2 mL/min).
MS 258 [M−H]$^−$ (ES−).
$^1$H NMR δ(CDCl$_3$) 3.41 (2H, q), 3.58 (2H, s), 5.19 (2H, s), 7.30-7.42 (5H, m). Step 3: Benzyl 2-oxo-4-(2,2,2-trifluoroethyl)-2,3-dihydro-1,3-thiazole-5-carboxylate
Prepared according to J. Het. Chem. 22, 1985, 1621-30 using benzyl (2E)-3-amino-5,5,5-trifluoropent-2-enoate. Obtained as a pale yellow solid (0.61 g).
Retention time: 3.10 min (reverse phase analytical HPLC (Hewlett Packard Series 1100): Waters "Symmetry" C8 column 3.5 μm; 4.6×50 mm column gradient 0.1% ammonium acetate/acetonitrile 75% to 5% in 3 min; flow 2 mL/min).
MS 318 (ES+ve) [M+H]$^+$
$^1$H NMR δ(CDCl$_3$) 3.93 (2H, q), 5.28 (2H, s), 7.33-7.42 (5H, m), 9.47 (1H, s).

Step 4: 2-Oxo-4-(2,2,2-trifluoroethyl)-2,3-dihydro-1, 3-thiazole-5-carboxylic acid Benzyl 2-oxo-4-(2,2,2-trifluoroethyl)-2,3-dihydro-1,3-thiazole-5-carboxylate (0.6 g) in ethanol was treated with 5% palladium on carbon and hydrogenated at 3 bar for 8 days. After filtration, the solvent was evaporated to yield the title compound as a colourless oil (0.15 g).
Retention time: 0.37 min (reverse phase analytical HPLC (Hewlett Packard Series 1100):Waters "Symmetry" C8 column 3.5 μm; 4.6×50 mm column gradient 0.1% ammonium acetate/acetonitrile 95% to 50% in 3 min; flow 2 mL/min).
MS (ES−ve) 226 [M−H]$^−$ Step 5: N-{(2R)-3-[4-(3,4-Dichlorophenoxy)piperidin-1-yl]-2-hydroxypropyl}-2-oxo-4-(2,2,2-trifluoroethyl)-2,3-dihydro-1,3-thiazole-5-carboxamide Prepared as Example 4. Obtained as a white solid (0.12 g).
The title compound has a pKa 6.6 (measured using Method B).
MS (APCI+ve) 528/530 [M+H]$^+$
$^1$H NMR δ(DMSO-d$_6$) 1.56-1.68 (2H, m), 1.86-1.96 (2H, m), 2.23-2.39 (4H, m), 2.65-2.79 (2H, m), 3.09-3.27 (2H, m), 3.73 (1H, quintet), 3.97 (2H, q), 4.44 (1H, septet), 4.75 (1H, s), 6.98 (1H, dd), 7.26 (1H, d), 7.49 (1H, d), 7.81 (1H, t).

EXAMPLE 34

N-{(2R)-3-[4-(3,4-Dichlorophenoxy)piperidin-1-yl]-2-hydroxypropyl}-2-oxo-4-pyridin-2-yl-2,3-dihydro-1,3-thiazole-5-carboxamide

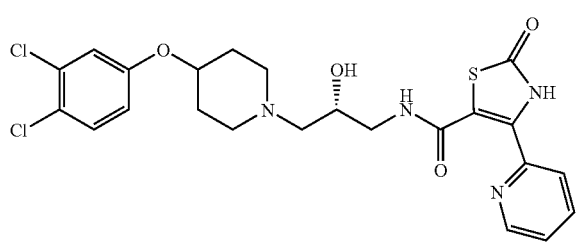

Step 1: Ethyl (2E)-3-amino-3-pyridin-2-yl acrylate

Prepared as Example 33 Step 2 using ethyl 3-oxo-3-pyridin-2-ylpropanoate to yield the title compound as a brown oil (2.5 g).
Retention time: 2.92 min (reverse phase analytical HPLC (Hewlett Packard Series 1100): Waters "Symmetry" C8 column 3.5 μm; 4.6×50 mm column gradient 0.1% ammonium acetate/acetonitrile 95% to 50% in 3 min; flow 2 mL/min).
$^1$H NMR δ(CDCl$_3$) 1.32 (3H, t), 4.21 (2H, q), 5.34 (1H, s), 7.34 (1H, ddd), 7.75 (2H, td), 8.63 (1H, dt).

Step 2: Ethyl 2-oxo-4-pyridin-2-yl-2,3-dihydro-1,3-thiazole-5-carboxylate

Prepared according to J. Het. Chem. 22, 1985, 1 621-30.
MS (ES+ve) 251 [M+H]$^+$
$^1$H NMR δ(DMSO-d$_6$) 1.08 (3H, t), 4.09 (2H, q), 7.51 (1H, ddd), 7.82 (1H, dt), 7.92 (1H, td), 8.67 (1H, dq), 12.32 (1H, s).

Step 3: 2-Oxo-4-pyridin-2-yl-2,3-dihydro-1,3-thiazole-5-carboxylic acid

Prepared as for Example 4 to yield the title compound as a pale yellow solid.
Retention time: 0.49 min (reverse phase analytical HPLC (Hewlett Packard Series 1100): Waters "Symmetry" C8 column 3.5 μm; 4.6×50 mm column gradient 0.1% ammonium acetate/acetonitrile 95% to 50% in 3 μm; flow 2 mL/min).
MS (ES+ve) 223 [M+H]$^+$ Step 4: N-{(2R)-3-[4-(3,4-Dichlorophenoxy)piperidin-1-yl]-2-hydroxypropyl}-2-oxo-4-pyridin-2-yl-2,3-dihydro-1,3-thiazole-5-carboxamide Prepared as Example 15, Step 2 to yield the title compound as a white solid (0.032 g).
The title compound has pKa 7.1 (calculated using ACD).
MS (APCI+ve) 523/525(M+H)$^+$
$^1$H NMR δ(DMSO-d$_6$) 1.52-1.65 (2H, m), 1.82-1.94 (2H, m), 2.20-2.34 (4H, m), 2.61-2.73 (2H, m), 3.05-3.17 (1H, m), 3.42 (1H, dt), 3.72 (1H, quintet), 4.42 (1H, septet), 4.83 (1H, s), 6.97 (1H, dd), 7.25 (1H, d), 7.49 (1H, d), 7.56 (1H, dd), 7.85 (1H, d), 8.04 (1H, td), 8.71 (1H, d), 10.85 (1H, s), 11.96 (1H, s).

EXAMPLE 35

N-{(2R)-3-[4-(3,4-Dichlorophenoxy)piperidin-1-yl]-2-hydroxypropyl}-6-oxo-2-(pentafluoroethyl)-1,6-dihydropyridine-3-carboxamide

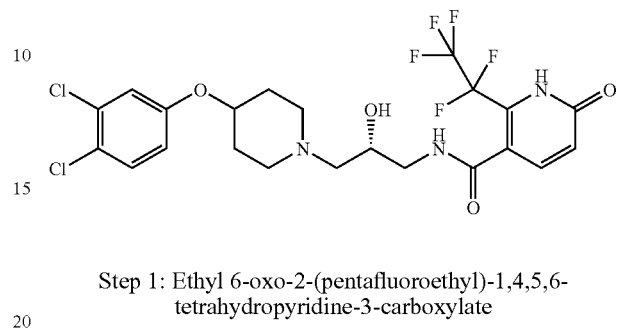

Step 1: Ethyl 6-oxo-2-(pentafluoroethyl)-1,4,5,6-tetrahydropyridine-3-carboxylate A suspension of acrylamide (4.11 g), ethyl 4,4,5,5,5-pentafluoro-3-oxopentanoate (16.5 g) and p-toluenesulphonic acid (0.120 g) in chlorobenzene (40 mL) was sonicated for 30 minutes then heated by microwave irradiation (150 W, 120° C.) for 3 h. The reaction mixture was concentrated in vacuo and subjected to flash column chromatography (eluent 1:3 ethyl acetate/isohexane) to yield a colourless solid (0.697 g).
MS (ES-ve) 286 [M-H]$^+$
$^1$H NMR δ(CDCl$_3$) 7.13 (s, 1H), 4.25 (q, J=7.2 Hz, 2H), 2.79-2.73 (m, 2H), 2.62-2.57 (m, 2H), 1.30 (t, J=7.1 Hz, 3H).

Step 2: Ethyl 6-oxo-2-(pentafluoroethyl)-1,6-dihydropyridine-3-carboxylate

A suspension of ethyl 6-oxo-2-(pentafluoroethyl)-1,4,5,6-tetrahydropyridine-3-carboxylate (0.690 g) and N-bromosuccinimide (0.427 g) in carbon tetrachloride (5 mL) was heated at 80° C. for 20 h. The reaction mixture was concentrated in vacuo and subjected to flash column chromatography (eluent 1:3 ethyl acetate/isohexane) to yield a colourless solid (0.30 g).
MS (ES-ve) 284 [M-H]$^-$
$^1$H NMR δ(CDCl$_3$) 1.36 (3H, t), 4.37 (2H, q), 6.93 (1H, d), 7.90 (1H, d).

Step 3: 6-Oxo-2-(pentafluoroethyl)-1,6-dihydropyridine-3-carboxylic acid

A suspension of ethyl 6-oxo-2-(pentafluoroethyl)-1,6-dihydropyridine-3-carboxylate (0.300 g) in concentrated hydrochloric acid (10 mL) was heated at reflux for 20 h. The reaction mixture was cooled and a colourless solid filtered off (0.30 g).
MS (ES-ve) 256 [M-H]$^-$
$^1$H NMR δ(DMSO-d$_6$) 6.98 (1H, d), 8.04 (1H, d), 12.03 (1H, s).

Step 4: N-{(2R)-3-[4-(3,4-Dichlorophenoxy)piperidin-1-yl]-2-hydroxypropyl}-6-oxo-2-(pentafluoroethyl)-1,6-dihydropyridine-3-carboxamide A stirred solution of 6-oxo-2-(pentafluoroethyl)-1,6-dihydropyridine-3-carboxylic acid (0.105 g) in thionyl chloride (5 mL) was heated at reflux for 3 h. Thionyl chloride was removed from the cooled solution in vacuo. The residue was dissolved in THF (4 mL) and this solution was added drop wise at room temperature to a solution of (2R)-1-amino-3-[4-(3,4-dichlorophenoxy)piperidin-1-yl]propan-2-ol (0.130 g) and triethylamine (0.4 mL) in DCM (5 mL) before stirring overnight. The reaction mixture was concentrated in vacuo and redissolved in 9:1 acetonitrile/water (4 mL) before subjecting to RPHPLC (gradient 0.1% ammonium acetate/acetonitrile 95% to 50%) to yield the title compound as a white solid (125 mg).

The title compound has pKa 6.3 (calculated using ACD).

MS (ES+ve) 558/560 [M+H]$^+$ $^1$H NMR δ(CD$_3$OD) 1.69-1.79 (2H, m), 1.90-1.99 (2H, m), 2.48-2.60 (4H, m), 2.81-2.91 (2H, m), 3.26 (1H, dd), 3.35 (1H, dd), 3.87-3.93 (1H, m), 4.34-4.39 (1H, m), 6.77 (1H, d), 6.81 (1H, dd), 7.02 (1H, d), 7.29 (1H, d), 7.64 (1H, d).

EXAMPLE 36

N-{(2R)-3-[4-(3,4-Dichlorophenoxy)piperidin-1-yl]-2-hydroxypropyl}-5-(methylthio)-1H-1,2,3-triazole-4-carboxamide

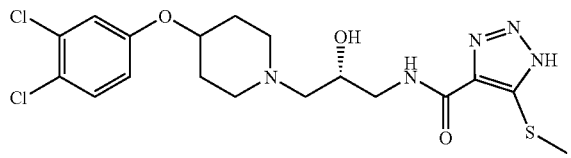

To a stirred suspension of 5-(methylthio)-1H-1,2,3-triazole-4-carboxylic acid [*J. Chem. Soc. Perkin. Trans.* 1 1982, 627] (0.085 g) in DCM (2 mL) was added oxalyl chloride (0.09 mL) then DMF (1 drop). The reaction mixture was stirred at room temperature for 1 h. The reaction mixture was concentrated in vacuo and the residue was dissolved in THF (2 mL) and this solution was added dropwise at room temperature to a solution of (2R)-1-amino-3-[4-(3,4-dichlorophenoxy)piperidin-1-yl]propan-2-ol (0.169 g) and triethylamine (0.22 mL) in DCM (5 mL). After being stirred for 1 h the reaction mixture was concentrated in vacuo and redissolved in methanol (4 mL) before being subjected to RPHPLC (gradient 0.1% ammonium acetate/acetonitrile 95% to 50%) to yield a white solid (0.091 g).

The title compound has a pKa 5.5 (measured using Method B).

MS (ES+ve) 460/462 [M+H]$^+$ $^1$H NMR δ(CD$_3$OD) 1.76-1.88 (2H, m), 1.93-2.06 (2H, m), 2.45 (3H, s), 2.63-2.77 (4H, m), 2.92-3.04 (2H, m), 3.35 (2H, t), 3.91-3.99 (1H, m), 4.38-4.46 (1H, m), 6.82 (1H, dd), 7.05 (1H, d), 7.30 (1H, d).

EXAMPLE 37

N-{(2R)-3-[4-(3,4-Dichlorophenoxy)piperidin-1-yl]-2-hydroxypropyl}-2-oxo-4-(trifluoromethyl)-2,3-dihydro-1,3-oxazole-5-carboxamide

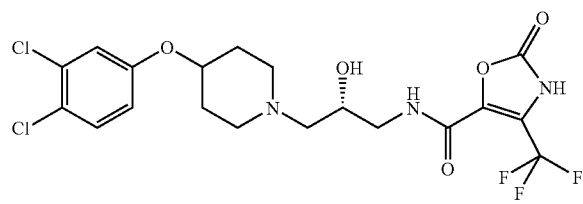

Ethyl 2-oxo-4-(trifluoromethyl)-2,3-dihydro-1,3-oxazole-5-carboxylate (0.3 g) [EP 0 027 020 A1] was treated with a solution of lithium hydroxide dissolved in 3:1 THF/water (6 mL), and heated at 50° C. for 1 h. The reaction mixture was partitioned between water (10 mL) and ethyl acetate (10 mL). The aqueous phase was acidified to pH 3 using dilute hydrochloric acid, followed by extraction with ethyl acetate (3×10 mL). The organics were combined and washed with water (2×10 mL) and brine (10 mL), then dried (Na$_2$SO$_4$), filtered, and concentrated in vacuo to leave the acid as an off white solid (0.175 g). Purification was carried out on amine resin by flushing with methanol to remove impurities, followed by 5% formic acid in methanol to isolate the product.

A stirred solution of 2-oxo-4-(trifluoromethyl)-2,3-dihydro-1,3-oxazole-5-carboxylic acid (0.032 g) in thionyl chloride (4 mL) was heated at reflux for 2 h. Excess thionyl chloride was removed from the cooled solution in vacuo. The residue was dissolved in THF (2 mL) and this solution was added dropwise at room temperature to a solution of (2R)-1-amino-3-[4-(3,4-dichlorophenoxy)piperidin-1-yl]propan-2-ol (0.051 g) and triethylamine (0.24 mL) in DCM (1 mL) before being stirred overnight.

The reaction mixture was concentrated in vacuo, and the residue was redissolved in acetonitrile containing 2-3 drops each of water, methanol and acetic acid before it was subjected to RPHPLC Novapak (gradient 0.1% ammonium acetate/acetonitrile 95% to 50%), followed by normal phase elution with 3/17 mixture of 7 N NH$_3$ in methanol/dichloromethane. This yielded the desired product as a yellow solid (0.016 g).

The title compound has pKa 5.8 (calculated using ACD).

MS (ES–ve) 498/496 [M–H]$^-$ $^1$H NMR δ(CD$_3$OD) 1.77 (s, 1H), 2.07 (s, 1H), 2.94-2.91 (m, 1H), 3.02-2.98 (m, 1H), 3.18-3.06 (m, 3H), 3.42-3.36 (m, 3H), 3.74-3.69 (m, 1H), 4.62 (quintet, 1H), 5.25 (s, 1H), 5.43 (s, 1H), 5.53 (s, 1H), 5.70 (s, 1H), 6.95 (dd, 2.8 Hz, 1H), 7.18 (d, 1H), 7.40 (d, 1H).

EXAMPLE 38

N-{(2R)-3-[4-(3,4-Dichlorophenoxy)piperidin-1-yl]-2-hydroxypropyl}-5-(trifluoromethyl)-1H-1,2,3-triazole-4-carboxamide

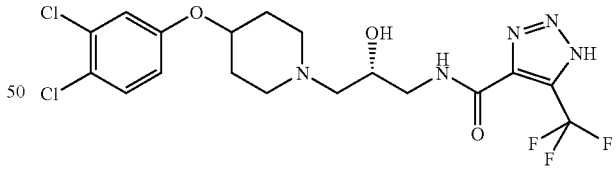

Step 1:
5-(Trifluoromethyl)-1H-1,2,3-triazole-4-carboxylic acid

Ethyl 5-(trifluoromethyl)-1H-1,2,3-triazole-4-carboxylate (0.312 g) was stirred in aqueous N sodium hydroxide (3.8 mL) and heated under reflux for 90 min. The cooled solution was acidified with aqueous hydrochloric acid and extracted with ethyl acetate. The extracts were washed with brine then dried and evaporated to leave a colourless solid (0.226 g).

MS (ES–ve) 180 [M–H]$^-$

Step 2: N-{(2R)-3-[4-(3,4-Dichlorophenoxy)piperidin-1-yl]-2-hydroxypropyl}-5-(trifluoromethyl)-1H-1,2,3-triazole-4-carboxamide Prepared by the method of Example 8 to give the title compound (0.113 g).
The title compound has a pKa 4.0 (measured using Method B).
MS (APCI+ve) 482/484/486 [M+H]+
$^1$H NMR δ(CD$_3$OD) 2.04 (4H, m), 2.99 (1H, m), 3.13 (3H, m), 3.32 (2H, m), 3.39 (2H, m), 4.10 (1H, m), 4.58 (1H, m), 6.88 (1H, dd), 7.13 (1H, d), 7.34 (1H, d).

EXAMPLE 39

N-{(2R)-3-[4-(3,4-Dichlorophenoxy)piperidin-1-yl]-2-hydroxypropyl}-5-[methyl(methyl sulfonyl)amino]-1H-1,2,3-triazole-4-carboxamide

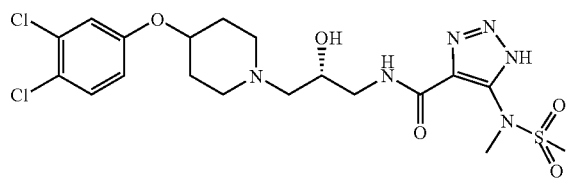

Step 1: Ethyl 5-amino-1-(4-methoxybenzyl)-1H-1,2,3-triazole-4-carboxylate

Ethyl cyanoacetate (1.96 mL) was added to a solution of sodium ethoxide, prepared from sodium (0.423 g) and ethanol (45 mL), and the solution was stirred for 30 min. A solution of 4-methoxybenzylazide (3.0 g) in ethanol (5 mL) was added dropwise and the mixture was heated under reflux for 5 h. The cooled mixture was poured into water and acidified with dilute hydrochloric acid then extracted with ethyl acetate. The extracts were washed with water, brine and evaporated. Purification by flash chromatography (ethyl acetate/dichloromethane 1:9 then 15:85) gave the product as a pale yellow solid (0.85 g).
MS (APCI-ve) 275 [M-H]+

Step 2: 1-(4-Methoxybenzyl)-5-[(methylsulfonyl)amino]-1H-1,2,3-triazole-4-carboxylic acid Ethyl 5-amino-1-(4-methoxybenzyl)-1H-1,2,3-triazole-4-carboxylate (0.85 g) and methane sulphonyl chloride (0.72 mL) were stirred in pyridine (20 mL) for 4 d. Further methane sulphonyl chloride (0.72 mL) was added and stirring continued for 24 h. Further methane sulphonyl chloride (0.5 mL) was added and stirring continued for 24 h. The mixture was concentrated in vacuo. The residue was suspended in dilute hydrochloric acid and extracted with ethyl acetate. The extracts was washed with dilute hydrochloric acid and water then evaporated. The residue was taken up in ethanol (70 mL) and 2 M sodium hydroxide solution (70 mL) and stirred for 18 h. The mixture was concentrated to about half volume and acidified with dilute hydrochloric acid. The mixture was extracted with ethyl acetate and the extracts were washed with water and brine, then dried and evaporated to leave a white solid (0.90 g).
$^1$H NMR δ(CD$_3$OD) 3.15 (3H, s), 3.79 (3H, s), 5.63 (2H, s), 6.92 (2H, d), 7.32 (2H, d).

Step 3: Methyl 1-(4-methoxybenzyl)-5-[methyl(methylsulfonyl)amino]-1H-1,2,3-triazole-4-carboxylate 1-(4-Methoxybenzyl)-5-[(methylsulfonyl)amino]-1H-1,2,3-triazole-4-carboxylic acid (0.9 g) and potassium carbonate (1.15 g) were stirred in dry DMF (10 mL). Methyl iodide (0.83 mL) was added and the mixture was stirred for 5 h. The mixture was poured onto water and extracted with ethyl acetate. The extracts were washed with dilute hydrochloric acid, water and brine then dried and evaporated. Purification by flash chromatography (ethyl acetate/DCM 1:9) afforded the sub-titled compound as a brown solid (0.54 g).
MS (APCI+ve) 355 [M+H]+

Step 4: Methyl 5-[methyl(methylsulfonyl)amino]-1H-1,2,3-triazole-4-carboxylate

Methyl 1-(4-methoxybenzyl)-5-[methyl(methylsulfonyl)amino]-1H-1,2,3-triazole-4-carboxylate (0.54 g) was stirred in trifluoroacetic acid (5 mL) at 60° C. for 6 h. The mixture was evaporated and the residue was co-evaporated with toluene. Purification by flash chromatography (1:49 methanol/DCM) gave the subtitle compound as a gum (0.36 g).
MS (APCI+ve) 235 [M+H]+

Step 5: 5-[Methyl(methylsulfonyl)amino]-1H-1,2,3-triazole-4-carboxylic acid

Methyl 5-[methyl(methylsulfonyl)amino]-1H-1,2,3-triazole-4-carboxylate (0.36 g) was stirred in THF (5 mL) with 2 N aqueous sodium hydroxide solution (1.7 mL) for 18 h. The mixture was concentrated in vacuo. To the aqueous residue was added dilute acetic acid and this was extracted with ethyl acetate (2×15 mL). The extracts were washed with water and brine then dried and evaporated to leave the subtitle compound (0.07 g).
MS (APCI-ve) 219 [M-H]-

Step 6: N-{(2R)-3-[4-(3,4-dichlorophenoxy)piperidin-1-yl]-2-hydroxypropyl}-5-[methyl(methylsulfonyl)amino]-1H-1,2,3-triazole-4-carboxamide Prepared using 5-[methyl(methylsulfonyl)amino]-1H-1,2,3-triazole-4-carboxylic acid (0.07 g) by the method of Example 8 to give the title compound (0.25 g).
The title compound has pKa 4.2 (calculated using ACD).
MS (APCI-ve) 519 [M-H]-
$^1$H NMR δ(CD$_3$OD) 1.95-2.06 (2H, m), 2.08-2.22 (2H, m), 2.94 (1H, m), 3.01 (1H, m), 3.06 (3H, s), 3.07-3.15 (1H, m), 3.18-3.29 (3H, m), 3.33 (3H, s), 3.49 (2H, d), 4.12 (1H, m), 4.60 (1H, m), 6.94 (1H, dd), 7.18 (1H, d), 7.41 (1H, d).

EXAMPLE 40

N-{(2R)-3-[4-(3-Chloro-4-cyano-2-methylphenoxy)piperidin-1-yl]-2-hydroxypropyl}-2-oxo-4-(trifluoromethyl)-2,3-dihydro-1,3-thiazole-5-carboxamide

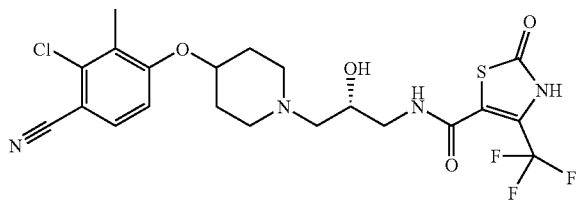

Step 1: 2-Chloro-4-hydroxy-3-methylbenzonitrile

A stirred solution of 4-bromo-3-chloro-2-methylphenol (0.427 g), zinc cyanide (0.271 g), and tetrakis[triphenylphosphine]palladium (0.056 g) in N-methyl-2-pyrrolidinone (5 mL) was heated under microwave irradiation (150 W) at 130° C. for 35 min. The reaction mixture was filtered through anhydrous magnesium sulfate, partitioned between 1:2 ethyl acetate/diethyl ether (15 mL) and water (15 mL). The aqueous phase was re-extracted with 1:2 ethyl acetate/diethyl ether (2×15 mL). The organics were combined, washed with water (2×20 mL), dried over anhydrous magnesium sulfate, filtered and concentrated in vacuo. The compound was purified by column chromatography using 1:9 ethyl acetate/iso-hexane as eluent, to give the desired product as a peach coloured solid (174 mg, 54%).

Retention time: 1.60 min (reverse phase analytical HPLC (Hewlett Packard Series 1100): Waters "Symmetry" C8 column 3.5 μm; 4.6×50 mm column gradient 0.1% ammonium acetate/acetonitrile 75% to 5% in 3 min; flow 2 mL/min).

MS (ES−ve) 166/168 [M−H]+

$^1$H NMR δ (CD$_3$OD) 2.27 (s, 3H), 6.82 (d, J=8.5 Hz, 1H), 7.44 (d, J=8.8 Hz, 1H).

Step 2: tert-Butyl 4-(3-chloro-4-cyano-2-methylphenoxy)piperidine-1-carboxylate Prepared according to method in patent WO 0220484 A1.

Retention time: 2.83 min (reverse phase analytical HPLC (Hewlett Packard Series 1100): Waters "Symmetry" C8 column 3.5 μm; 4.6×50 mm column gradient 0.1% ammonium acetate/acetonitrile 75% to 5% in 3 min; flow 2 mL/min).

$^1$H NMR δ(CDCl$_3$) 1.48 (s, 9H), 1.86-1.75 (m, 2H), 1.99-1.89 (m, 2H), 2.32 (s, 3H), 3.51-3.42 (m, 2H), 3.65-3.57 (m, 2H), 4.64-4.57 (m, 1H), 6.80 (d, J=8.7 Hz, 1H), 7.49 (d, J=8.7 Hz, 1H)

Step 3: 2-Chloro-3-methyl-4-(piperidin-4-yloxy)benzonitrile

Prepared according to Preparation 1, Step 2.

Retention time: 1.17 min (reverse phase analytical HPLC (Hewlett Packard Series 1100): Waters "Symmetry" C8 column 3.5 μm; 4.6×50 mm column gradient 0.1% ammonium acetate/acetonitrile 75% to 5% in 3 min; flow 2 mL/min).

MS (ES+ve) 251/253 [M+H]+

$^1$H NMR δ(CDCl$_3$) 1.80-1.70 (m, 2H), 2.06-1.96 (m, 2H), 2.32 (s, 3H), 2.83-2.75 (m, 2H), 3.18-3.09 (m, 2H), 4.54-4.47 (m, 1H), 6.79 (d, J=8.9 Hz, 1H), 7.47 (d, J=8.7 Hz, 1H).

Step 4: 4-({1-[(2R)-3-Amino-2-hydroxypropyl]piperidin-4-yl}oxy)-2-chloro-3-methylbenzonitrile Prepared according to Preparation 1, Step 3.

Retention time: 1.20 min (reverse phase analytical HPLC (Hewlett Packard Series 1100): Waters "Symmetry" C8 column 3.5 μm; 4.6×50 mm column gradient 0.1% ammonium acetate/acetonitrile 75% to 5% in 3 min; flow 2 mL/min).

MS (ES+ve) 324/326 [M+H]+

$^1$H NMR δ(CDCl$_3$) 1.29-1.22 (m, 2H), 1.94-1.81 (m, 2H), 2.08-1.95 (m, 2H), 2.31 (s, 3H), 2.31 (s, 3H), 2.46-2.33 (m, 3H), 2.67-2.59 (m, 3H), 2.90-2.80 (m, 2H), 3.73-3.66 (m, 1H), 4.51-4.44 (m, 1H), 6.79 (d, J=8.8 Hz, 1H), 7.47 (d, J=8.7 Hz, 1H).

Step 5: N-{(2R)-3-[4-(3-Chloro-4-cyano-2-methylphenoxy)piperidin-1-yl]-2-hydroxypropyl}-2-oxo-4-(trifluoromethyl)-2,3-dihydro-1,3-thiazole-5-carboxamide Prepared according to method for Example 4.

Retention time: 1.18 min (reverse phase analytical HPLC (Hewlett Packard Series 1100): Waters "Symmetry" C8 column 3.5 μm; 4.6×50 mm column gradient 0.1% ammonium acetate/acetonitrile 75% to 5% in 3 min; flow 2 mL/min).

The title compound has a pKa of 4.7 (measured using Method B) and pKa 6.1 (calculated using ACD).

MS (ES+ve) 519/521 [M+H]+, (ES−ve) 517/519 [M−H]−

$^1$H NMR δ (DMSO-d$_6$) 1.81-1.91 (m, 2H), 2.02-2.10 (m, 2H), 2.33 (s, 3H), 2.54-2.70 (m, 4H), 2.88-2.95 (m, 2H), 3.24-3.31 (m, 1H), 3.34-3.41 (m, 1H), 3.87 (quintet, 1H), 4.63-4.69 (m, 1H), 7.17 (d, 1H), 7.54-7.64 (m, 1H), 7.68 (d, 1H).

EXAMPLE 41

N-{(2R)-3-[4-(3-Chloro-4-cyanophenoxy)piperidin-1-yl]-2-hydroxypropyl}-5-(trifluoromethyl)-1H-1,2,3-triazole-4-carboxamide

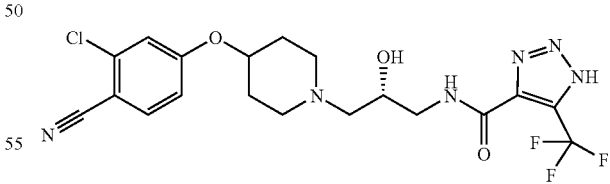

Prepared by the method of Example 31 to give the title compound (0.64 g).

The title compound has pKa 2.1 (calculated using ACD).

MS (APCI+ve) 473/475 [M+H]+

$^1$H NMR δ(CD$_3$OD) 2.39-2.67 (4H, m), 3.44 (1H, m), 3.55-3.90 (6H, m), 3.84 (1H, m), 7.45 (1H, dd), 7.65 (1H, d), 8.08 (1H, d).

EXAMPLE 42

2-Chloro-5-[({(2R)-3-[4-(3,4-dichloro-2-methylphenoxy)piperidin-1-yl]-2-hydroxypropyl}amino)carbonyl]benzoic acid

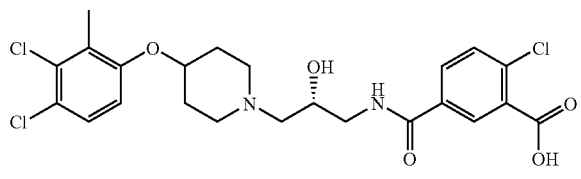

Step 1: 3-tert-Butyl 1-methyl 4-chloroisophthalate tert-Butyl 5-bromo-2-chlorobenzoate (1.9 g) (WO2003095430) was dissolved in methanol (18 ml) with N,N-diisopropylethylamine (2 mL) and dichlorobis(triphenylphosphine)-palladium(II) (0.134 g). The mixture was carbonylated at 85° C. for 12 h. The cooled solution was evaporated and purified by flash chromatography, eluting with 5:95 ethyl acetate/isohexane, to yield the subtitle compound as a colourless oil (0.67 g).

$^1$H NMR δ(CDCl$_3$) 1.62 (9H, s), 3.94 (3H, s), 7.49 (1H, dd), 8.02 (1H, dd), 8.35 (1H, d).

Step 2: 3-(tert-Butoxycarbonyl)-4-chlorobenzoic acid 3-tert-Butyl 1-methyl 4-chloroisophthalate (0.37 g) in THF (5 mL) was treated with lithium hydroxide (0.17 g) in water (5 mL) and the mixture was stirred for 18 h. The solvent was evaporated. Water and ethyl acetate were added. The aqueous extract was separated and acidified with dilute hydrochloric acid. The product was extracted into ethyl acetate. The solution was dried over sodium sulphate, filtered and the solvent was evaporated to yield the subtitle compound as a white solid (0.32 g).

Retention time: 1.98 min (reverse phase analytical HPLC (Hewlett Packard Series 1100): Waters "Symmetry" C8 column 3.5 μm; 4.6×50 mm column gradient 0.1% ammonium acetate/acetonitrile 95% to 50% in 3 min; flow 2 mL/min).

MS (ES−ve) 255 [M−H]−

$^1$H NMR δ(DMSO-d$_6$) 1.56 (9H, s), 7.69 (1H, d), 8.03 (1H, dd), 8.18 (1H, d).

Step 3: tert-Butyl 2-chloro-5-[({(2R)-3-[4-(3,4-dichloro-2-methylphenoxy)piperidin-1-yl]-2-hydroxypropyl}amino)carbonyl]benzoate Prepared as for Example 15, Step 2 and the sub-titled compound was obtained as a colourless oil (0.14 g).

Retention time: 2.93 min (reverse phase analytical HPLC (Hewlett Packard Series 1100): Waters "Symmetry" C8 column 3.5 μm; 4.6×50 mm column gradient 0.1% ammonium acetate/acetonitrile 75% to 5% in 3 min; flow 2 mL/min).

MS (ES+ve) 571 [M+H]+

Step 4: 2-Chloro-5-[({(2R)-3-[4-(3,4-dichloro-2-methylphenoxy)piperidin-1-yl]-2-hydroxypropyl}amino)carbonyl]benzoic acid tert-Butyl 2-chloro-5-[({(2R)-3-[4-(3,4-dichloro-2-methylphenoxy)piperidin-1-yl]-2-hydroxypropyl}amino)carbonyl]benzoate (0.14 g) in DCM (5 mL) was treated with trifluoroacetic acid (1.5 mL) and the mixture was stirred for 1.5 h. The solvent was evaporated. The product was purified by RPHPLC (Symmetry, 0.1% ammonium acetate/acetonitrile) to yield the title compound as a white solid. (0.05g).

The title compound has a measured pKa 2.3, and a calculated pKa 2.6 (calculated using ACD).

MS (APCI−ve) 513/517[M−H]−

$^1$H NMR δ(CD$_3$OD+NaOD) 1.79-1.91 (2H, m), 1.98-2.09 (2H, m), 2.34 (3H, s), 2.47-2.58 (2H, m), 2.52 (2H, d), 2.75-2.87 (2H, m), 3.43 (1H, dd), 3.53 (1H, dd), 4.02 (1H, quintet), 4.44-4.53 (1H, m), 6.95 (1H, d), 7.31 (1H, d), 7.49 (1H, d), 7.77 (1H, dd), 7.96 (1H, d).

EXAMPLE 43

4-Chloro-3-[({(2R)-3- [4-(3,4-dichloro-2-methylphenoxy)piperidin-1-yl]-2-hydroxypropyl}amino)carbonyl]benzoic acid

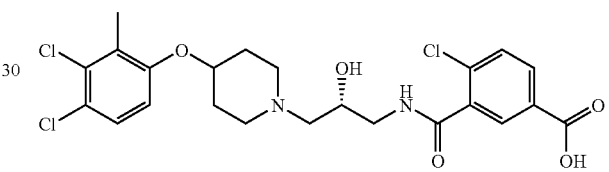

Step 1: Methyl 4-chloro-3-[({(2R)-3-[4-(3,4-dichloro-2-methylphenoxy)piperidin-1-yl]-2-hydroxypropyl}amino)carbonyl]benzoate Prepared as for Example 15, Step 2 using 2-chloro-5-(methoxycarbonyl)benzoic acid (FR2842805) and (2R)-1-amino-3-[4-(3,4-dichloro-2-methylphenoxy)piperidin-1-yl]propan-2-ol and was obtained as a colourless oil (0.1 g).

Retention time: 2.42 min (reverse phase analytical HPLC (Hewlett Packard Series 1100): Waters "Symmetry" C8 column 3.5 μm; 4.6×50 mm column gradient 0.1% ammonium acetate/acetonitrile 75% to 5% in 3 min; flow 2 mL/min).

MS (ES−ve) 529/531 [M−H]−

Step 2: 4-Chloro-3-[({(2R)-3-[4-(3,4-dichloro-2-methylphenoxy)piperidin-1-yl]-2-hydroxypropyl}amino)carbonyl]benzoic acid Prepared as for Example 23, Step 3 and obtained as white solid (0.022 g).

The title compound has pKa 3.7 (calculated using ACD).

MS (APCI−ve) 513/517[M−H]−

$^1$H NMR δ(CD$_3$OD) 1.78-1.89 (2H, m), 1.97-2.08 (2H, m), 2.34 (3H, s), 2.47-2.62 (4H, m), 2.79-2.90 (2H, m), 3.49 (2H, ddd), 4.03 (1H, quintet), 4.46 (1H, septet), 6.95 (1H, d), 7.30 (1H, d), 7.48 (1H, d), 8.00 (1H, dd), 8.06 (1H, d).

EXAMPLE 44

4-Chloro-3-[2-({(2R)-3-[4-(3,4-dichloro-2-methylphenoxy)piperidin-1-yl]-2-hydroxypropyl}amino)-2-oxoethoxy]benzoic acid

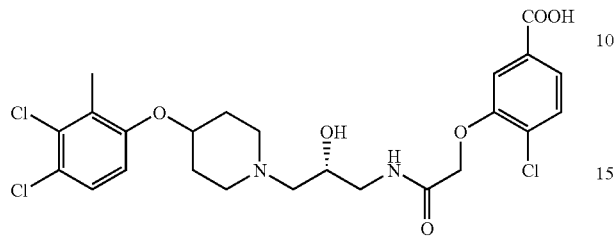

Step 1: Methyl 3-(2-tert-butoxy-2-oxoethoxy)-4-chlorobenzoate

Methyl 4-chloro-3-hydroxybenzoate [*Chem. Pharm. Bull.* 1994, 42(11),2365-9] (0.73 g), caesium carbonate (1.27 g) and tert butylbromoacetate (0.58 mL) in DMF (6 mL) were heated and stirred at 60° C. for 3 h. Water was added and the product was extracted into ethyl acetate. The extracts were dried over sodium sulphate, filtered and the solvent was evaporated. The resulting oil was purified by flash chromatography, using 1:10 ethyl acetate/isohexane as eluent, to yield the subtitle compound as a colourless oil (1.25 g).

$^1$H NMR δ(CDCl$_3$) 1.49 (9H, s), 3.91 (3H, s), 4.66 (2H, s), 7.45 (1H, d), 7.48 (1H, d), 7.62 (1H, dd).

Step 2: [2-Chloro-5-(methoxycarbonyl)phenoxy]acetic acid

Prepared as Example 42 Step 4 to yield the subtitle compound as an off white solid (0.18 g).

$^1$H NMR δ(DMSO-d$_6$) 3.86 (3H, s), 4.93 (2H, s), 7.48 (1H, d), 7.56 (1H, dd), 7.62 (1H, d), 13.21 (1H, s).
MS (ES−ve) 243 [M−H]$^-$

Step 3: Methyl 4-chloro-3-[2-({(2R)-3-[4-(3,4-dichloro-2-methylphenoxy)piperidin-1-yl]-2-hydroxypropyl}amino)-2-oxoethoxy]benzoate Prepared as for Example 15 Step 2 using [2-Chloro-5-(methoxycarbonyl)-phenoxy]acetic acid and (2R)-1-amino-3-[4-(3,4-dichloro-2-methylphenoxy)piperidin-1-yl]propan-2-ol to yield the subtitle compound as a colourless oil (0.084 g).

MS (ES+ve) 561/3 [M+H]$^+$

Retention time: 2.58 min (reverse phase analytical HPLC (Hewlett Packard Series 1100): Waters "Symmetry" C8 column 3.5 μm; 4.6×50 mm column gradient 0.1% ammonium acetate/acetonitrile 75% to 5% in 3 min; flow 2 mL/min).

Step 4: 4-Chloro-3-[2-({(2R)-3-[4-(3,4-dichloro-2-methylphenoxy)piperidin-1-yl]-2-hydroxypropyl}amino)-2-oxoethoxy]benzoic acid Prepared as for Example 23, Step 3. The title compound was obtained as a white solid (0.02 g).
The title compound has pKa 3.8 (calculated using ACD).
MS (APCI−ve) 545/547[M−H]$^-$ $^1$H NMR δ(CD$_3$OD) 1.98-2.13 (2H, m), 2.16-2.31 (2H, m), 2.34 (3H, s), 2.94-3.11 (2H, m), 3.15-3.26 (2H, m), 3.34 (2H, s), 3.40 (2H, d), 4.10-4.17 (1H, m), 4.64-4.70 (1H, m), 4.71 (2H, d), 6.99 (1H, d), 7.32 (1H, d), 7.41 (1H, d), 7.58 (1H, dd), 7.59 (1H, s).

EXAMPLE 45

{2-Chloro-5-[({(2R)-3-[4-(3,4-dichloro-2-methylphenoxy)piperidin-1-yl]-2-hydroxypropyl}amino)carbonyl]phenoxy}acetic acid

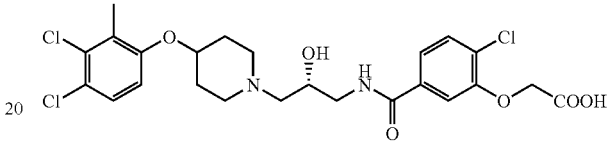

Step 1: 3-(2-tert-Butoxy-2-oxoethoxy)-4-chlorobenzoic acid

Methyl 3-(2-tert-butoxy-2-oxoethoxy)-4-chlorobenzoate (0.7 g) in 9:1 tert butanol:water was subjected to Antarctica B lipase for 6 d. Filtration and evaporation of the solvent yielded the subtitle compound as an off-white solid (0.6 g).

MS (ES−ve) 285 [M−H]$^-$ $^1$H NMR δ(DMSO-d$_6$) 1.42 (9H, s), 4.88 (2H, s), 7.45 (1H, d), 7.54 (1H, dd), 7.58 (1H, d).

Step 2: tert-Butyl{2-chloro-5-[({(2R)-3-[4-(3,4-dichloro-2-methylphenoxy)piperidin-1-yl]-2-hydroxypropyl}amino)carbonyl]phenoxy}acetate Prepared as for Example 15, Step 2 using 3-(2-tert-butoxy-2-oxoethoxy)-4-chlorobenzoic acid and (2R)-1-amino-3-[4-(3,4-dichloro-2-methylphenoxy)piperidin-1-yl]propan-2-ol to yield the subtitle compound as a colourless oil (0.14 g).

MS (ES+ve) 603/5 [M+H]$^+$

Retention time: 2.98 min (reverse phase analytical HPLC (Hewlett Packard Series 1100): Waters "Symmetry" C8 column 3.5 μm; 4.6×50 mm column gradient 0.1% ammonium acetate/acetonitrile 75% to 5% in 3 min; flow 2 mL/min).

Step 3: {2-Chloro-5-[({(2R)-3-[4-(3,4-dichloro-2-methylphenoxy)piperidin-1-yl]-2-hydroxypropyl}amino)carbonyl]phenoxy}acetic acid Prepared as Example 42 Step 4 to yield the title compound as a white solid (0.085 g).

The title compound has pKa 3.0 (calculated using ACD).
MS (APCI−ve) 543/547[M−H]$^-$ $^1$H NMR δ(CD$_3$OD+NaOD) 1.74-1.86 (2H, m), 1.95-2.05 (2H, m), 2.31 (3H, s), 2.41-2.52 (4H, m), 2.74-2.84 (2H, m), 3.32-3.38 (1H, m), 3.50 (1H, dd), 3.98 (1H, quintet), 4.42 (1H, septet), 4.54 (2H, s), 6.91 (1H, d), 7.27 (1H, d), 7.37 (1H, dd), 7.38 (1H, s), 7.44 (1H, d).

EXAMPLE 46

3-[2-({(2R)-3-[4-(3,4-Dichloro-2-methylphenoxy)piperidin-1-yl]-2-hydroxypropyl}amino)-2-oxoethoxy]benzoic acid

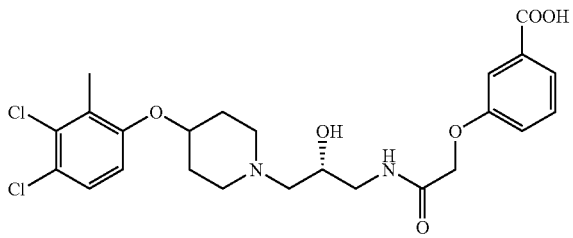

Step 1: Methyl 3-[2-({(2R)-3-[4-(3,4-dichloro-2-methylphenoxy)piperidin-1-yl]-2-hydroxypropyl}amino)-2-oxoethoxy]benzoate Prepared as for Example 15, Step 2 using [3-(methoxycarbonyl)phenoxy]acetic acid [*Asian Journal of Chemistry* 1992, 4(4), 920-3] and (2R)-1-amino-3-[4-(3,4-dichloro-2-methylphenoxy)piperidin-1-yl]propan-2-ol to yield the subtitle compound as a pale yellow oil (0.11 g).

MS (ES+ve) 525/527 [M+H]$^+$

Retention time: 2.35 min (reverse phase analytical HPLC (Hewlett Packard Series 1100): Waters "Symmetry" C8 column 3.5 µm; 4.6×50 mm column gradient 0.1% ammonium acetate/acetonitrile 75% to 5% in 3 min; flow 2 mL/min).

Step 2: 3-[2-({(2R)-3-[4-(3,4-Dichloro-2-methylphenoxy)piperidin-1-yl]-2-hydroxypropyl}amino)-2-oxoethoxy]benzoic acid Prepared as for Example 23, Step 3. The title compound was obtained as a white solid (0.049 g).

The title compound has a measured pKa 2.6 and a calculated pKa 4.0 (calculated using ACD).

MS (APCI−ve) 509/511 [M−H]$^−$ $^1$H NMR δ(CD$_3$OD+NaOD) 1.73-1.85 (2H, m), 1.94-2.03 (2H, m), 2.30 (3H, s), 2.33-2.47 (4H, m), 2.68-2.78 (2H, m), 3.32-3.44 (2H, m), 3.90 (1H, quintet), 4.37-4.46 (1H, m), 4.57 (2H, s), 6.92 (1H, d), 7.04-7.08 (1H, m), 7.24-7.34 (2H, m), 7.56-7.61 (2H, m).

EXAMPLE 47

{3-[({(2R)-3-[4-(3,4-Dichloro-2-methylphenoxy)piperidin-1-yl]-2-hydroxypropyl}amino)carbonyl]phenoxy}acetic acid

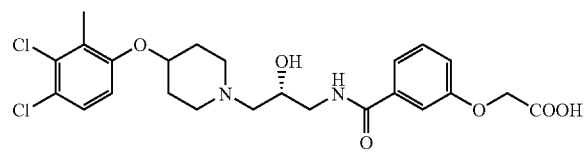

Step 1: tert-Butyl{3-[({(2R)-3-[4-(3,4-dichloro-2-methylphenoxy)piperidin-1-yl]-2-hydroxypropyl}amino)carbonyl]phenoxy}acetate Prepared as for Example 15 Step 2 using 3-(2-tert-butoxy-2-oxoethoxy)benzoic acid [WO 00/78317 A1] and (2R)-1-amino-3-[4-(3,4-dichloro-2-methylphenoxy)piperidin-1-yl]propan-2-ol to yield the subtitle compound as a white solid (0.11 g).

MS (ES+ve) 567/569 [M+H]$^+$

Retention time: 2.65 min (reverse phase analytical HPLC (Hewlett Packard Series 1100): Waters "Symmetry" C8 column 3.5 µm; 4.6×50 mm column gradient 0.1% ammonium acetate/acetonitrile 75% to 5% in 3 min; flow 2 mL/min).

Step 2: {3-[({(2R)-3-[4-(3,4-Dichloro-2-methylphenoxy)piperidin-1-yl]-2-hydroxypropyl}amino)carbonyl]phenoxy}acetic acid Prepared as Example 42, Step 4 to yield the title compound as a white solid (0.063 g).

The title compound has pKa 3.1 (calculated using ACD).

MS (APCI+ve) 511/513 [M+H]$^+$ $^1$H NMR δ(CD$_3$OD+NaOD) 1.75-1.87 (2H, m), 1.96-2.05 (2H, m), 2.31 (3H, s), 2.42-2.54 (4H, m), 2.75-2.85 (2H, m), 3.37 (1H, dd), 3.50 (1H, dd), 3.99 (1H, quintet), 4.47 (3H, s), 6.91 (1H, d), 7.08-7.12 (1H, m), 7.27 (1H, dd), 7.32-7.40 (3H, m).

EXAMPLE 48

Pharmacological Analysis: Calcium flux [Ca$^{2+}$]$_i$ assay

Human Eosinophils

Human eosinophils were isolated from EDTA anticoagulated peripheral blood as previously described (Hansel et al., *J. Immunol. Methods*, 1991, 145, 105-110). The cells were resuspended (5×10$^6$ ml$^{-1}$) and loaded with 5 µM FLUO-3/AM+Pluronic F127 2.2 µl/ml (Molecular Probes) in low potassium solution (LKS; NaCl 118 mM, MgSO$_4$ 0.8 mM, glucose 5.5 mM, Na$_2$CO$_3$ 8.5 mM, KCl 5 mM, HEPES 20 mM, CaCl$_2$ 1.8 mM, BSA 0.1%, pH 7.4) for one hour at room temperature. After loading, cells were centrifuged at 200 g for 5 min and resuspended in LKS at 2.5×10$^6$ ml$^{-1}$. The cells were then transferred to 96 well FLIPr plates (Poly-D-Lysine plates from Becton Dickinson pre-incubated with 5 µM fibronectin for two h) at 25 µl/well. The plate was centrifuged at 200 g for 5 min and the cells were washed twice with LKS (200 µl; room temperature).

A compound of the Examples was pre-dissolved in DMSO and added to a final concentration of 0.1% (v/v) DMSO. Assays were initiated by the addition of an A$_{50}$ concentration of eotaxin and the transient increase in fluo-3 fluorescence (1$_{Ex}$=490 nm and 1$_{Em}$=520 nm) monitored using a FLIPR (Fluorometric Imaging Plate Reader, Molecular Devices, Sunnyvale, U.S.A.).

Compounds of the Examples were found to be antagonists if the increase in fluorescence induced by eotaxin (a selective CCR3 agonist) was inhibited in a concentration dependent manner. The concentration of antagonist required to inhibit the fluorescence by 50% can be used to determine the IC$_{50}$ for the antagonist at the CCR3 receptor.

EXAMPLE 49

Human Eosinophil Chemotaxis

Human eosinophils were isolated from EDTA anticoagulated peripheral blood as previously described (Hansel et al., J. Immunol. Methods, 1991, 145, 105-110). The cells were resuspended at 10×10⁶ ml⁻¹ in RPMI containing 200 IU/ml penicillin, 200 µg/ml streptomycin sulfate and supplemented with 10% HIFCS, at room temperature.

Eosinophils (700 µl) were pre-incubated for 15 mins at 37° C. with 7 µl of either vehicle or compound (100× required final concentration in 10% DMSO). The chemotaxis plate (ChemoTx, 3 µm pore, Neuroprobe) was loaded by adding 28 µl of a concentration of eotaxin 0.1 to 100 nM (a selective CCR3 agonist over this concentration range) containing a concentration of a compound according to the Examples or solvent to the lower wells of the chemotaxis plate. The filter was then placed over the wells and 25 µl of eosinophil suspension were added to the top of the filter. The plate was incubated for 1 hr at 37° C. in a humidified incubator with a 95% air/5% $CO_2$ atmosphere to allow chemotaxis.

The medium, containing cells that had not migrated, was carefully aspirated from above the filter and discarded. The filter was washed once with phosphate buffered saline (PBS) containing 5 mM EDTA to remove any adherent cells. Cells that had migrated through the filter were pelleted by centrifugation (300 ×g for 5 mins at room temperature) and the filter removed and the supernatant transferred to each well of a 96-well plate (Costar). The pelleted cells were lysed by the addition of 28 µl of PBS containing 0.5% Triton ×100 followed by two cycles of freeze/thawing. The cell lysate was then added to the supernatant. The number of eosinophils migrating was quantified according to the method of Strath et al., J. Immunol. Methods, 1985, 83, 209 by measuring eosinophil peroxidase activity in the supernatant.

Compounds of the Examples were found to be antagonists of eotaxin mediated human eosinophil chemotaxis if the concentration response to eotaxin was shifted to the right of the control curve. Measuring the concentration of eotaxin required to give 50% chemotaxis in the presence or absence of compounds enables the apparent affinity of the compounds at CCR3 to be calculated, or the assay can be used to determine activity of compounds at a set concentration of compound against a predefined concentration of eotaxin.

EXAMPLE 50

Guinea-pig Isolated Trachea (See for example, Harrison, R. W. S., Carswell, H. & Young, J. M. (1984) European J. Pharmacol., 106, 405-409.)

Male albino Dunkin-Hartley guinea-pigs (250 g) were killed by cervical dislocation and the whole trachea removed. After clearing the adherent connective tissue, the trachea was cut into six ring segments each three cartilage bands wide and then suspended in 20 ml organ baths containing Krebs-Henseleit solution of the following composition (mM): NaCl 117.6, $NaH_2PO_4$ 0.9, $NaHCO_3$ 25.0, $MgSO_4$ 1.2, KCl 5.4, $CaCl_2$ 2.6 and glucose 11.1. The buffer was maintained at 37° C. and gassed with 5% $CO_2$ in oxygen. Indomethacin (2.8 µM) was added to the Krebs solution to prevent development of smooth muscle tone due to the synthesis of cyclo-oxygenase products. The tracheal rings were suspended between two parallel tungsten wire hooks, one attached to an Ormed beam isometric force transducer and the other to a stationary support in the organ bath. Changes in isometric force were recorded on 2-channel Sekonic flat bed chart recorders.

Experimental Protocols

At the beginning of each experiment a force of 1 g was applied to the tissues and this was reinstated over a 60 minute equilibration period until a steady resting tone was achieved. Subsequently, a cumulative histamine concentration effect (E/[A]) curve was constructed at 0.5 $\log_{10}$ unit increments, in each tissue. The tissues were then washed and approximately 30 minutes later, test compound or vehicle (20% DMSO) was added. Following an incubation period of 60 minutes a second E/[A] curve was performed to histamine.

Contraction responses were recorded as a percentage of the first curve maximum.

Data Analysis

Experimental E/[A] curve data were analysed for the purposes of estimating the potencies (p[$A_{50}$] values) of histamine in the absence and presence of the test compound. Affinity (p$A_2$) values of test compounds were subsequently calculated using the following equation:

$$\log(r-1)=\log[B]+pA_2$$

where r=[$A$]$_{50}$ in presence of test compound/[$A$]$_{50}$ in absence of antagonist and [B] is the concentration of test compound. Compounds of the Examples were found to be H1 antagonists.

EXAMPLE 51

Histamine H1 receptor binding activity of compounds of the invention was assessed by competition displacement of 1 nM [3H]-pyrilamine (Amersham, Bucks, Product code TRK 608, specific activity 30 Ci/mmol) to 2 µg membranes prepared from recombinant CHO-K1 cells expressing the human H1 receptor (Euroscreen SA, Brussels, Belgium, product code ES-390-M) in assay buffer (50 mM Tris pH 7.4 containing 2 mM $MgCl_2$, 250 mM sucrose and 100 mM NaCl) for 1 hour at room temperature.

The following compounds of the invention gave inhibition of [3H]pyrilimine binding:

| Example | H1 pKi |
|---------|--------|
| 5 | 6.9 |
| 8 | 7.8 |
| 10 | 6.9 |
| 14 | 6.9 |
| 16 | 7.6 |
| 18 | 6.5 |
| 20 | 6.7 |
| 24 | 7.7 |
| 25 | 7.8 |
| 27 | 6.6 |
| 28 | 7.4 |
| 31 | 6.8 |
| 37 | 6.7 |
| 39 | 6.9 |
| 42 | 6.9 |
| 44 | 7.9 |
| 45 | 7.2 |

The invention claimed is:

1. N- {(2R)-3-[4-(3,4-Dichlorophenoxy)piperidin-1-yl]-2-hydroxypropyl} -2,3 -dihydro-2-oxo-4-(trifluoromethyl)-5-thiazolecarboxamide, or a pharmaceutically acceptable salt thereof.

2. A pharmaceutical composition comprising a compound or a pharmaceutically acceptable salt thereof, as claimed in claim 1, and a pharmaceutically acceptable adjuvant, diluent or carrier therefor.

* * * * *

UNITED STATES PATENT AND TRADEMARK OFFICE
CERTIFICATE OF CORRECTION

| | | |
|---|---|---|
| PATENT NO. | : 7,956,070 B2 | Page 1 of 1 |
| APPLICATION NO. | : 10/587633 | |
| DATED | : June 7, 2011 | |
| INVENTOR(S) | : Lilian Alcaraz et al. | |

It is certified that error appears in the above-identified patent and that said Letters Patent is hereby corrected as shown below:

Column 1, line 10, "tiled" should read -- filed --;

Column 56, lines 56-57 (approx.), "N- {(2R)-3-[4-(3 ,4-Dichlorophenoxy)piperidin- 1-yl]-2-hydroxypropyl} -2,3 -dihydro" should read -- N-{(2R)-3-[4-(3,4-Dichlorophenoxy)piperidin-1-yl]-2-hydroxypropyl}-2,3-dihydro --;

Signed and Sealed this
Twenty-fifth Day of October, 2011

David J. Kappos
*Director of the United States Patent and Trademark Office*